US009452139B2

(12) United States Patent
Hartman et al.

(10) Patent No.: US 9,452,139 B2
(45) Date of Patent: Sep. 27, 2016

(54) RESPIRABLE AGGLOMERATES OF POROUS CARRIER PARTICLES AND MICRONIZED DRUG

(71) Applicants: Michael Hartman, Millbrae, CA (US); Thomas E Tarara, Burlingame, CA (US); Patrick Teung, Sunnyvale, CA (US); Jeffry G Weers, Belmont, CA (US)

(72) Inventors: Michael Hartman, Millbrae, CA (US); Thomas E Tarara, Burlingame, CA (US); Patrick Teung, Sunnyvale, CA (US); Jeffry G Weers, Belmont, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/202,262

(22) Filed: Mar. 10, 2014

(65) Prior Publication Data
US 2014/0302147 A1 Oct. 9, 2014

Related U.S. Application Data

(60) Provisional application No. 61/784,842, filed on Mar. 14, 2013.

(51) Int. Cl.
*A61K 9/16* (2006.01)
*A61K 45/06* (2006.01)
(Continued)

(52) U.S. Cl.
CPC ........... *A61K 9/1617* (2013.01); *A61K 9/0075* (2013.01); *A61K 9/145* (2013.01); *A61K 9/1682* (2013.01); *A61K 31/40* (2013.01);
(Continued)

(58) Field of Classification Search
None
See application file for complete search history.

(56) References Cited

U.S. PATENT DOCUMENTS 2,956,062 A 10/1960 Lunsford
3,991,761 A 11/1976 Cocozza
(Continued)

FOREIGN PATENT DOCUMENTS

EP 0258238 A1 3/1988
WO 8605991 A1 10/1986
(Continued)

OTHER PUBLICATIONS

R Vehring, D Lechuga-Ballesteros, V Joshi, B Noga, SK Dwivedi. "Cosuspensions of Microcrystals and Engineered Microparticles for Uniform and Efficient Delivery of Respiratory Therapeutics from Pressurized Metered Dose Inhalers." Langmuir, vol. 28, 2012, pp. 15015-15023, published Sep. 17, 2012.*

(Continued)

*Primary Examiner* — Isaac Shomer
(74) *Attorney, Agent, or Firm* — Daniel Woods

(57) ABSTRACT

Embodiments of the present invention provide a dry powder composition comprising porous carrier particles associated with one, two, three or more micronized drugs or APIs wherein an ordered mixture between the micronized drug or drugs and the carrier particle results, such that the micronized drug or drugs adhere strongly to the carrier particles forming a stable ordered mixture of respirable agglomerates. Embodiments of the present invention further comprise a spray-drying process to create the respirable agglomerates. Embodiments of the present invention further relate to the use of the dry powder formulation comprising respirable agglomerates for the treatment of a patient having a disease or condition which is treatable thereby.

18 Claims, 7 Drawing Sheets

(51) Int. Cl.
*A61K 47/02* (2006.01)
*A61K 9/00* (2006.01)
*A61K 47/24* (2006.01)
*A61K 9/14* (2006.01)
*A61K 31/40* (2006.01)
*A61K 31/4704* (2006.01)
*A61K 31/58* (2006.01)

(52) U.S. Cl.
CPC ........... *A61K31/4704* (2013.01); *A61K 31/58* (2013.01); *A61K 45/06* (2013.01); *A61K 47/02* (2013.01); *A61K 47/24* (2013.01); *Y10S 514/826* (2013.01)

(56) References Cited

U.S. PATENT DOCUMENTS

| | | | |
|---|---|---|---|
| 4,472,393 | A | 9/1984 | Shapiro |
| 5,889,015 | A | 3/1999 | Sequeira et al. |
| 6,057,307 | A | 5/2000 | Sequeira et al. |
| 6,057,581 | A | 5/2000 | Doan |
| 6,307,060 | B1 | 10/2001 | Noe et al. |
| 6,365,581 | B1 | 4/2002 | Sequeira et al. |
| 6,536,427 | B2 | 3/2003 | Davies et al. |
| 6,565,885 | B1 | 5/2003 | Tarara et al. |
| 6,613,795 | B2 | 9/2003 | Noe et al. |
| 6,677,322 | B2 | 1/2004 | Sequeira et al. |
| 6,677,323 | B2 | 1/2004 | Sequeira et al. |
| 7,442,388 | B2 | 10/2008 | Weers et al. |
| 7,559,325 | B2 | 7/2009 | Dunkley et al. |
| 7,871,598 | B1 | 1/2011 | Dellamary et al. |
| 8,069,851 | B2 | 12/2011 | Dunkley et al. |
| 9,050,267 | B2 * | 6/2015 | Weers .................. A61K 9/0075 |
| 2004/0171550 | A1 * | 9/2004 | Backstrom et al. ............ 514/12 |
| 2005/0183724 | A1 | 8/2005 | Gumaste et al. |
| 2007/0295332 | A1 | 12/2007 | Ziegler et al. |
| 2009/0209502 | A1 * | 8/2009 | Haeberlin et al. ............ 514/171 |
| 2010/0108058 | A1 | 5/2010 | Glusker et al. |
| 2012/0039817 | A1 * | 2/2012 | Vehring .................. A61K 9/008 424/43 |

FOREIGN PATENT DOCUMENTS

| | | |
|---|---|---|
| WO | 9300123 A1 | 1/1993 |
| WO | 9414492 A2 | 7/1994 |
| WO | 9609085 A1 | 3/1996 |
| WO | 9725086 A2 | 7/1997 |
| WO | 9730743 A2 | 8/1997 |
| WO | 0021594 A2 | 4/2000 |
| WO | 0072904 A1 | 12/2000 |
| WO | 0075114 A1 | 12/2000 |
| WO | 0143530 A2 | 6/2001 |
| WO | 03061743 A1 | 7/2003 |
| WO | 03077979 A1 | 9/2003 |
| WO | 2004054556 | 7/2004 |
| WO | 2005014089 A1 | 2/2005 |
| WO | 2005037353 A1 | 4/2005 |
| WO | 2005123684 A2 | 12/2005 |
| WO | 2008000839 A1 | 1/2008 |
| WO | 2012106575 | 8/2012 |

OTHER PUBLICATIONS

Supplementary Material for R Vehring, D Lechuga-Ballesteros, V Joshi, B Noga, SK Dwivedi. "Cosuspensions of Microcrystals and Engineered Microparticles for Uniform and Efficient Delivery of Respiratory Therapeutics from Pressurized Metered Dose Inhalers." Langmuir, vol. 28, 2012, published Sep. 17, 2012, 5 printed pages.*
PW Jones, N Barnes, C Vogelmeier, D Lawrence, B Kramer. "Efficacy of indacaterol in the treatment of patients with COPD." Primary Care Respiratory Journal, vol. 20(4), 2011, pp. 380-388.*
SM Berge, LD Bighley, DC Monkhouse. "Pharmaceutical Salts." Journal of Pharmaceutical Sciences, vol. 66 No. 1, Jan. 1977, pp. 1-19.*
K Chapman, CM Fogarty, C Peckitt, C Lassen, D Jadayel, J Dederichs, M Dalvi, B Kramer. "Delivery characteristics and patients' handling of two single-dose dry-powder inhalers used in COPD." International Journal of COPD, vol. 6, 2011, pp. 353-363.*
European Medicines Agency, "Assessment Report, Seebri Breezhaler." Procedure: EMEA/H/C/002430. Aug. 1, 2012, 84 total pages.*
M Hoppentocht, P Hagedoorn, HW Frijlink, AH de Boer. "Technological and Practical Challenges of Dry Powder Inhalers and Formulations." Advanced Drug Delivery Reviews, vol. 75, 2014, pp. 18-31.*
MY Yang, JGY Chan H-K Chan. "Pulmonary Drug Delivery by Powder Aerosols." Journal of Controlled Release, vol. 193, 2014, pp. 228-240.*
MJ Telko, AJ Hickey. "Dry Powder Inhaler Formulation." Respiratory Care, vol. 50 No. 9, Sep. 2005, pp. 1209-1227.*
Francesca Buttini et al: "Particles and powders: Tools of innovation for non-invasive drug administration", Journal of Controlled Release, Elsevier, Amsterdam, NL, vol. 161, No. 2, Feb. 27, 2012, pp. 693-702, XP028492694.
David E. Geller et al: "Development of an Inhaled Dry-Powder Formulation of Tobramycin Using PulmoSphere (TM) Technology" Journal of Aerosol Medicine and Pulmonary Drug Delivery, vol. 24, No. 4, Aug. 2011, pp. 175-182, XP05512137.
Reinhard Vehring et al: "Cosuspensions of Microcrystals and Engineered Microparticles for Uniform and Efficient Delivery of Respiratory Therapeutics from Pressurized Metered Dose Inhalers", Langmuir, vo I . 28, No. 42, Sep. 17, 2012, pp. 15015-15023, XP055121915.
Anders Bjerg et al: "The future of combining inhaled drugs for COPD", Current Opinion in Pharmacology, vol. 12, No. 3, Jun. 2012, pp. 252-255, XP055121358.
"Powder mixture" downloaded from https://en.wikipedia.org/wiki/Powder_mixture Dec. 10, 2015.
Jones et al., "Efficacy of indacaterol in the treatment of patients with COPD", Primary Care Respiratory Journal, 2011, vol. 20, No. 4, pp. 380-388.
Berge et al., "Pharmaceutical Salts", Journal of Pharmaceutical Sciences, 1977, vol. 66, No. 1, pp. 1-19.
Telko et al., "Dry Powder Inhaler Formulation", Respiratory Care, 2005, vol. 50, No. 9, pp. 1209-1227.

* cited by examiner

RESPIRABLE AGGLOMERATES OF POROUS CARRIER PARTICLES AND MICRONIZED DRUG

FIELD OF THE INVENTION

The disclosure relates to physically stable and substantially uniform dry powder medicament formulations of one, two, three, or more active ingredients that are useful for pulmonary administration, and in particular for administering medicaments to treat diseases of the lung.

BACKGROUND

Active pharmaceutical ingredients (APIs) that are useful for treating respiratory diseases are often formulated for administration pulmonarily, to wit: by inhalation, such as with portable inhalers. Pulmonary drug delivery methods and compositions that effectively provide the pharmaceutical compound at the specific site of action (the lung) potentially serve to minimize toxic side effects, lower dosing requirements, and decrease therapeutic costs. The development of such systems for pulmonary drug delivery has long been a goal of the pharmaceutical industry.

Inhalation systems commonly used to deliver drugs locally to the pulmonary air passages are dry powder inhalers (DPIs), metered dose inhalers (MDIs), and nebulizers. DPIs generally rely entirely on the patient's inspiratory efforts to introduce a medicament in a dry powder form to the lungs.

To achieve good deposition of aerosolized particles in the lungs, the particles should have an aerodynamic diameter in the respirable size range from 1 to 5 µm. However, fine particles of this size are highly cohesive with poor bulk powder properties (e.g., poor powder flow, fluidization, and dispersibility).

To improve bulk powder properties of dry powder aerosols, micronized drug particles are often blended with coarse lactose monohydrate carrier particles with a geometric diameter between 50 and 200 µm. The blend forms a mixture with the fine particles adhering to the carrier, and the mixture taking on the bulk powder characteristics of the coarse carrier particles.

Engineered particle blends require a delicate balance of surface forces. The adhesive force between the drug and carrier must be strong enough to create an ordered mixture that maintains its structure during filling and on storage, yet weak enough to allow the drug and carrier to separate during aerosol administration. The adhesive force between the fine particles and the carrier particles in current marketed products remains high, however, leading to mean lung delivery efficiencies of just 10-30% of the nominal dose, and mean interpatient variability in lung delivery of approximately 30-50%.

In practice, the engineered blends of micronized drug adhered to lactose carrier particles do not exist as simple ordered mixtures. Drug may be stuck to coarse lactose, to fine lactose, or to itself in large agglomerates. This led some to refer to these complex formulations as "multi-particulate nightmares". The interactions become even more complex for fixed dose combinations of two or more drugs. Each drug in the combination exhibits a different force of adhesion with the carrier, and a different dependence of drug dispersion from the carrier with flow rate. In addition, there are additional adhesive forces between the two drugs and between each drug and fine particle excipient. The complexity of the interactions can lead to variability in aerosol performance, with differences observed for each drug as a mono-component or in the fixed dose combination, and with differences in dose strength. The complex interactions between the various formulation components leads to difficulty in meeting the "combination rule", which relates that the in vitro aerosol performance of each drug should be equivalent for the drug alone and in combination. In order to overcome potential issues with meeting the combination rule with lactose blends, some groups have turned to sophisticated devices, where blends of each drug in the fixed dose combination is present in its own receptacle, and the two receptacles are aerosolized concurrently (see for example, Anderson et al., WO 2003/061743).

SUMMARY OF THE INVENTION

Accordingly, embodiments of the present invention overcome the complexity observed with standard blends of coarse lactose and micronized drug by creating ordered mixtures of respirable agglomerates comprising small porous carrier particles and micronized drug.

Embodiments of the present invention further provide a method for creating uniform ordered mixtures of respirable agglomerates of small porous particles and micronized drug, comprising preparing a suspension of drug and carrier in an anti-solvent, followed by removal of the anti-solvent in a drying process.

Embodiments of the present invention thus comprise a dry powder composition comprising carrier particles associated with one, two, three or more micronized drugs or APIs wherein an ordered mixture between the micronized drug or drugs and the carrier particle results, such that the micronized drug or drugs adhere strongly to the carrier particles forming stable respirable agglomerates. The carrier particles are small and/or porous.

Embodiments of the invention comprise a plurality of small porous carrier particles, together with a plurality of one or more small active drug particles which together form an ordered mixture of aerodynamically sized, pulmonarily-deliverable respirable agglomerates.

Embodiments of the present invention obviate the need for dispersion of the drug from the carrier during a patient's inhalation, and the patient instead inhales the respirable agglomerates of micronized drug and small porous carrier particles into their lungs. As such, the physicochemical properties of the drug substance and its content in the powder become largely irrelevant. This is in contrast to the conventional mixtures of coarse lactose and micronized drug, where both the adhesive forces between the drug and carrier, and the cohesive forces between the micronized drug particles are critical in the resulting bulk powder properties. Thus, the aerosol performance of the respirable agglomerates of embodiments of the present invention do not depend on a balance of adhesive and cohesive forces between carrier and drug particles, but instead depend only on the cohesive forces between the respirable agglomerates.

The cohesive forces between small porous carrier particles are significantly reduced relative to standard micronized drug particles, due to the decreased area of contact between particles afforded by the porous particle morphology, and the hydrophobic nature of the excipients enriched at the particle surface. As a result, small porous carrier particles have been shown to fluidize and disperse effectively at low peak inspiratory flow rates, reflecting the decreased interparticle cohesive forces engineered into these particles. The respirable agglomerates of micronized drugs and small porous carrier particles exhibit the same powder fluidization and dispersion behavior as the small porous carrier particles alone.

Embodiments of the present invention accordingly afford a composition and method to formulate fixed dose combinations of drugs as a dry powder comprising respirable agglomerates, wherein the composition and method are largely independent of whether the drug is present as a mono component, or in combination with a second or third drug substance. Thus embodiments of the present invention mitigate, reduce or eliminate variations in aerosol performance that occur as a result of co-formulation of two or more drugs in a single formulation. Embodiments of the present invention afford improved lung targeting (high mean lung delivery efficiencies) relative to standard blends with coarse lactose. This leads to decreases in drug deposition in the mouth-throat and systemic circulation for drugs that are orally bioavailable. Bypassing deposition in the mouth-throat also reduces interpatient variability in total lung delivery.

Embodiments of the present invention comprise a process to create the respirable agglomerates. Thus, in some embodiments, a dry powder comprising respirable agglomerates is achieved by creating a small and/or porous carrier particle, using a spray-drying process, then preparing a suspension of the desired drug or drugs and small carrier particle in an anti-solvent (e.g., perfluorooctyl bromide). The anti-solvent is then removed in a solvent removal step, such as by spray-drying, yielding the dry powder comprising respirable agglomerates.

Embodiments of the dry powder comprising respirable agglomerates, and process, of the present invention maintain a crystallinity of the drug substance through the manufacturing process and during storage for an extended period.

Adhesion of drug to the porous carrier particles is driven thermodynamically such that the drug particles favor minimal contact with the anti-solvent. The use of a porous carrier particle, that is, one with a high surface area, potentiates strong adhesion of drug to carrier. The strength of the adhesive force between drug and carrier particle is driven primarily by van der Waals forces, which are directly proportional to the diameter of the particles.

Removal of drug particles from the porous carrier particles during filling or on administration from a dry powder inhaler requires that hydrodynamic forces exerted on the respirable agglomerates exceed the adhesive (primarily van der Waals) forces. These forces (e.g., drag and lift forces) scale with the square of the particle diameter, whereas the van der Waals forces between drug and carrier scale with the diameter of the particles. For particles in the size range from about 1 to 5 microns (µm), the adhesive forces significantly exceed the fluid forces, resulting in poor dispersion of drug from carrier. This is often observed for neat micronized drug crystals or even micronized drug adhered to coarse lactose carrier particles, and was the driving force for blending with coarse lactose carrier particles in an effort to improve powder flow.

In process and composition embodiments of the present invention, stable respirable agglomerates are made by engineering to take advantage of these strong adhesive properties. The small size and porous nature of the resulting stable agglomerates leads to small aerodynamic (respirable) sizes and as a result, excellent aerosol delivery to the lungs.

Embodiments of respirable agglomerates, methods of making, methods of using, formulations and doses of the present invention afford advantages relative to conventional dry powder formulations. Such advantages include one or more of: (a) a monomodal aerodynamic particle size distribution (APSD) vs. a bimodal APSD for conventional blends; (b) an increase in lung targeting, with a resulting total lung deposition of from 50-70% for the respirable agglomerates compared to only 10-30% for lactose blends; (c) improvements in dose consistency resulting from reductions in mean variability in total lung deposition to 5-20% or less, compared to a variability of 30-50% for lactose blends; (d) improvements in dose consistency in fixed dose combinations (i.e., mono, combo, and triple formulations exhibit comparable APSD); (e) a manufacturing process which enables effective mixing of micron-sized particles with low variability in composition, and no observed segregation during filling, on storage, and during aerosol administration; (f) an ability to buffer the formulation, thereby enabling more effective control of chemical stability. One or more of these advantages results from nearly eliminating the large sized fraction of particles that deposit in the induction port and pre-separator in an impactor due to incomplete dispersion of drug from carrier. This leads to significant reductions in mouth-throat deposition in vivo, and advantageously decreases un-wanted systemic delivery for drugs.

Embodiments of respirable agglomerates, methods of making, methods of using, formulations and doses of the present invention provide compositions and methods which minimize a dissolved fraction of an API resulting in a corresponding minimization of potentially unstable amorphous API in the final product.

In a first aspect of the present invention, there is provided a dry powder composition comprising respirable agglomerates comprising engineered carrier particles in an ordered mixture with one, two, three or more different active ingredients. The active ingredients may be present in amorphous form but are often present in crystalline form.

The active ingredients can be any active pharmaceutical ingredients that are useful for treating diseases or conditions. The diseases or conditions may comprise pulmonary diseases or conditions, systemic diseases or conditions, or both. Exemplary diseases or conditions include obstructive or inflammatory airways disease, such as obstructive pulmonary disease (COPD), asthma, idiopathic pulmonary fibrosis, bronchiectasis, and cystic fibrosis as well as lung diseases such as pulmonary arterial hypertension.

Suitable active ingredients include long acting $\beta_2$-agonists such as salmeterol, formoterol, indacaterol and salts thereof, muscarinic antagonists such as tiotropium and glycopyrronium and salts thereof, and corticosteroids including budesonide, ciclesonide, fluticasone and mometasone and salts thereof. Suitable exemplary combinations include (indacaterol maleate and glycopyrronium bromide), (indacaterol acetate and glycopyrronium bromide), (indacaterol xinafoate and glycopyrronium bromide), (indacaterol maleate and mometasone furoate), (formoterol fumarate and budesonide), (salmeterol xinafoate and fluticasone propionate), (salmeterol xinafoate and tiotropium bromide), (formoterol fumarate and tiotropium bromide), (indacaterol maleate, mometasone furoate and glycopyrronium bromide), (indacaterol acetate, mometasone furoate and glycopyrronium bromide), (indacaterol xinafoate, mometasone furoate and glycopyrronium bromide) and (formoterol fumarate, fluticasone propionate and tiotropium bromide).

In a second aspect of the present invention, there is provided a powder composition comprising respirable agglomerates comprising small porous engineered carrier particles, having one or more of a MMD of about 1-10 microns, an MMAD of about 2-4 microns and a tapped density of about 0.03 to 0.5 g/cm$^3$; a first micronized active drug particle comprising indacaterol, a second micronized active drug particle comprising mometasone, and a third micronized active drug particle comprising glycopyrrolate as an ordered mixture with the carrier particle. Each of the micronized drug particles comprise an MMD of less than about 4 microns, such as about 0.1-3 microns. The active ingredients are preferably present in substantially (i.e., at least about 95%) in crystalline form.

In a third aspect of the present invention, there is provided a powder composition comprising respirable agglomerates comprising a $\beta_2$-agonist, a corticosteroid, small porous carrier particles, and optionally, an anti-muscarinic. In a further variation of this aspect, the actives are each present in an amount of from about 0.5-3% by weight, and the small porous carrier particles comprise a 2:1 molar ratio of DSPC: $CaCl_2$.

In a fourth aspect of the present invention, there is provided a powder composition comprising respirable agglomerates comprising at least one relatively water soluble drug active, at least one relatively water in-soluble drug active, and small porous carrier particles. In a further variation of this aspect, the actives are each present in an amount of from about 0.5-3% by weight, and the small porous carrier particles comprise a 2:1 molar ratio of DSPC: $CaCl_2$.

In a fifth aspect, the present invention relates to a process for preparing a respirable dry powder formulation of agglomerate particles, the process comprising the steps of:

(a) preparing a first feedstock comprising a hydrophobic excipient dispersed in an aqueous liquid phase and spray-drying said first feedstock to provide a bulk powder composition comprising a porous dry powder carrier particle;

(b) preparing at least a first active drug ingredient by micronizing the drug to provide particles having a mass median diameter (MMD) of less than about 4 microns;

(c) preparing a second feedstock comprising a suspension of the carrier particles of step (a) and the micronized drug particles of step (b) in a non-aqueous anti-solvent; and (d) subjecting the second feedstock to a solvent removal process to yield a bulk powder formulation comprising a plurality of respirable aggregate particles, wherein the respirable agglomerate particles comprise an ordered mixture of carrier particles and micronized drug particles. In this aspect, the hydrophobic excipient may further comprise DSPC and calcium chloride. In a still further version of this aspect, the micronized drug particles may have a size range of 1-3 microns. In a still further version of this aspect, the respirable agglomerates are characterized by an MMAD of about 2-4 microns and a tapped density of about 0.03 to 0.5 g/cm$^3$.

In a sixth aspect, the present invention relates to a process for preparing a respirable dry powder formulation of agglomerate particles, the process comprising the steps of:

(a) preparing a first feedstock comprising a hydrophobic excipient such as DSPC and calcium chloride in a molar ratio of 2:1 dispersed in an aqueous liquid phase and spray-drying said first feedstock to provide a plurality of small porous carrier particles;

(b) preparing at least a first, a second, and optionally, a third or more active drug ingredient by micronizing each drug to provide particles having a size of less than about 4 microns;

(c) preparing a second feedstock comprising the carrier particles of step (a) and the micronized drug particles of step (b) in a non-aqueous anti-solvent; and (d) subjecting the second feedstock to a solvent removal process to yield a dry powder comprising a plurality of respirable aggregate particles comprising an inhalable dry powder formulation. In a further version of this aspect, the first active comprises a beta adrenoreceptor agonist, such as indacaterol, the second active comprises an anti-inflammatory such as mometasone and the third active comprises an anti-muscarinic such as glycopyrrolate.

In a seventh aspect, the present invention relates to a method for the treatment of a patient, and/or the use of the dry powder formulation comprising respirable agglomerates according to any embodiments herein, which method and/or use comprises administering to a patient (or subject) having a disease or condition an effective amount of the dry powder formulation comprising respirable agglomerates according to any embodiments herein. Exemplary diseases or conditions include obstructive or inflammatory airways disease, such as obstructive pulmonary disease (COPD), asthma, idiopathic pulmonary fibrosis, bronchiectasis, and cystic fibrosis as well as lung diseases such as pulmonary arterial hypertension.

In a further aspect, a method of treatment comprises administering to a subject a dry powder formulation comprising respirable agglomerates comprising about 0.5-3% w/w indacaterol acetate, about 0.5-3% w/w mometasone furoate, about 0.5-3% w/w glycopyrronium bromide, and about 91-99% small porous carrier particles comprising about a 2:1 molar ratio of DSPC:$CaCl_2$.

In a further aspect, a method of treatment comprises administering to a subject a dry powder formulation comprising respirable agglomerates comprising about 0.5-3% w/w indacaterol acetate and about 0.5-3% w/w mometasone furoate, and about 94-99% small porous carrier particles comprising about a 2:1 molar ratio of DSPC:$CaCl_2$.

In a further aspect, a method of treatment comprises administering to a subject a dry powder formulation comprising respirable agglomerates comprising about 0.5-3% w/w indacaterol acetate and about 0.5-3% w/w glycopyrronium bromide, and about 94-99% small porous carrier particles comprising about a 2:1 molar ratio of DSPC:$CaCl_2$.

In a further aspect, the present invention relates to the aforementioned dry powder formulation comprising respirable agglomerates for use in the treatment of a disease or condition.

In a further aspect, the present invention relates to a delivery system that comprises an inhaler that contains one or more embodiments of the dry powder formulation comprising respirable agglomerates.

In a further aspect, the present invention relates to a unit dose that comprises a receptacle that contains one or more embodiments of the dry powder formulation comprising respirable agglomerates.

A still further aspect of the present invention comprises any two or more of the herein described aspects, embodiments or features.

TERMS

Terms used in the specification have the following meanings:

"Active ingredient", "therapeutically active ingredient", "active agent", "drug" or "drug substance" as used herein means the active ingredient of a pharmaceutical, also known as an active pharmaceutical ingredient (API).

"Fixed dose combination" as used herein refers to a pharmaceutical product that contains two or more active ingredients that are formulated together in a single dosage form available in certain fixed doses.

"Amorphous" as used herein refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ("glass transition").

"Crystalline" as used herein refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ("melting point"). In the context of the present invention, a crystalline active ingredient means an active ingredient with crystallinity of greater than 85%. In certain embodiments the crystallinity is suitably greater than 90%. In other embodiments the crystallinity is suitably greater than 95%.

"Solids Concentration" refers to the concentration of active ingredient(s) and excipients dissolved or dispersed in the liquid solution or dispersion to be spray-dried.

"Drug Loading" refers to the percentage of active ingredient(s) on a mass basis in the total mass of the formulation.

"% Dissolved" refers to percentage of a crystalline active ingredient which dissolves in the liquid feedstock to be spray-dried.

"Mass median diameter" or "MMD" or "x50" as used herein means the median diameter of a plurality of particles, typically in a polydisperse particle population, i.e., consisting of a range of particle sizes. MMD values as reported herein are determined by laser diffraction (Sympatec Helos, Clausthal-Zellerfeld, Germany), unless the context indicates otherwise.

"Rugous" as used herein means having numerous wrinkles or creases, i.e., being ridged or wrinkled.

"Rugosity" as used herein is a measure of the surface roughness of an engineered particle. For the purposes of this invention, rugosity is calculated from the specific surface area obtained from BET measurements, true density obtained from helium pycnometry, and the surface to volume ratio obtained by laser diffraction (Sympatec), viz:

$$\text{Rugosity} = (SSA \cdot \rho_{true})/S_v$$

where $S_v=6/D_{32}$, where $D_{32}$ is the average diameter based on unit surface area. Increases in surface roughness are expected to reduce interparticle cohesive forces, and improve targeting of aerosol to the lungs. Improved lung targeting is expected to reduce interpatient variability, and levels of drug in the oropharynx and systemic circulation. In one or more embodiments, the rugosity $S_v$ is from 3 to 20, e.g., from 5 to 10.

"Emitted Dose" or "ED" as used herein refers to an indication of the delivery of dry powder from an inhaler device after an actuation or dispersion event from a powder unit. ED is defined as the ratio of the dose delivered by an inhaler device to the nominal or metered dose. The ED is an experimentally determined parameter, and may be determined using an in vitro device set up which mimics patient dosing. It is sometimes also referred to as the Delivered Dose (DD). The ED is determined using a drug specific method such as high pressure liquid chromatography.

"Emitted Powder Mass" or "EPM" as used herein refers to the mass of a powder that is delivered from an inhaler device after an actuation or dispersion event from a powder unit. The EPM is measured gravimetrically.

"Mass median aerodynamic diameter" or "MMAD" as used herein refer to the median aerodynamic size of a plurality of particles, typically in a polydisperse population. The "aerodynamic diameter" is the diameter of a unit density sphere having the same settling velocity, generally in air, as a powder and is therefore a useful way to characterize an aerosolized powder or other dispersed particle or particle formulation in terms of its settling behaviour. The aerodynamic particle size distributions (APSD) and MMAD are determined herein by cascade impaction, using a NEXT GENERATION IMPACTOR™ (as described by United States Pharmacopeia <601> Appartutus 6). In general, if the particles are aerodynamically too large, fewer particles will reach the deep lung. If the particles are too small, a larger percentage of the particles may be exhaled.

"Fine particle fraction" or "FPF" as used herein means the mass of an active ingredient below a specified minimum aerodynamic size relative to the nominal dose. For example, $FPF_{<3.3 \, \mu m}$ refers to the percentage of the nominal dose which has an aerodynamic particle size less than 3.3 μm. FPF values are determined using cascade impaction, either on an ANDERSEN™ cascade impactor (as described by United States Pharmacopeia <601> Appartutus 6), or a NEXT GENERATION IMPACTOR™ cascade impactor. FPF values may also be expressed relative to an impactor device stage and/or the impactor device filter, meaning that the percentage of particles that remain in the designated stage. Thus $FPF_{S3-F}$ refers to that fraction of the nominal dose that remains on the stage 3 through the filter of the impactor device.

"Fine Particle Dose," or "FPD" as used herein means the dose (mass) of an active ingredient below a specified minimum aerodynamic size.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

The use of the term "about" to qualify a numerical range, qualifies all numbers within the range, unless the context indicates otherwise.

The entire disclosure of each United States and International patent or patent application mentioned in this patent specification is fully incorporated by reference herein for all purposes.

DETAILED DESCRIPTION OF THE DRAWINGS

The dry powder formulation of the present invention may be described with reference to the accompanying drawings. In those drawings.

Figure 3:
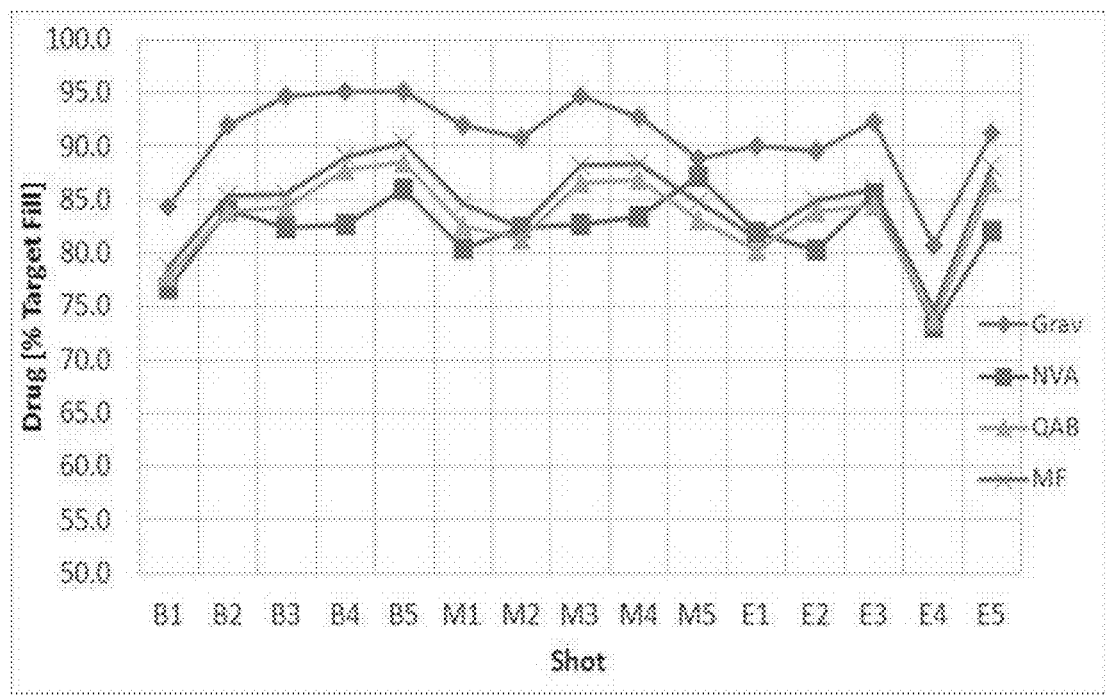

FIG. 3 is a graph showing delivered dose uniformity for a dry powder formulation comprising respirable agglomerates of indacaterol acetate, mometasone furoate, glycopyrronium bromide and small porous carrier particles made according to Example 1 (Lot 11015A-6-7). Filled capsules are assayed across the batch (i.e., at the beginning (B), middle (M), and end (E) of the filling process). Each drug is assayed by a drug specific method, and this is compared with the delivered dose determined gravimetrically.

Figure 4:
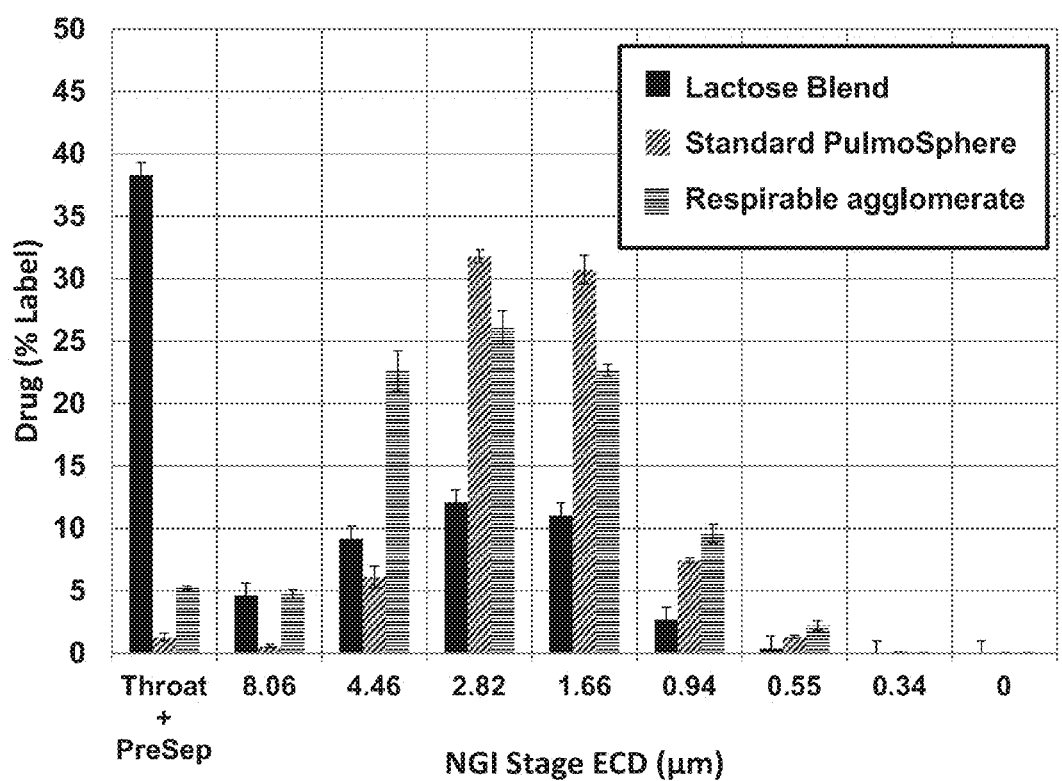

FIG. 4 is a graph comparing aerodynamic particle size distributions for respirable agglomerate dry powder formulation comprising indacaterol maleate made according to Example 1 (Lot 11015A-6-7) and manufactured by three discrete processes. The processes comprise a lactose blend as a commercial lot of OnBrez (Novartis); a standard PulmoSphere™ lot made using the suspension-based PulmoSphere manufacturing process, where the micronized indacaterol maleate is suspended in the emulsion-based feedstock and spray-dried; and the respirable agglomerates of Example 1.

Figure 5:
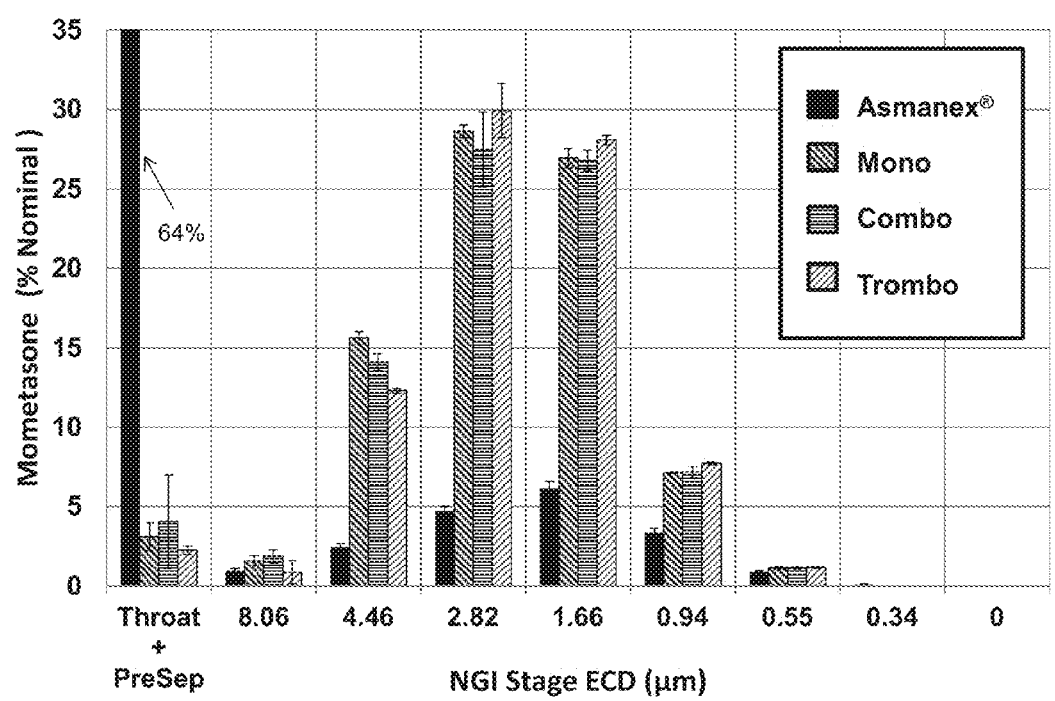

FIG. 5 is a graph of aerodynamic particle size distributions of dry powder respirable agglomerate formulations comprising mometasone furoate in comparison with the marketed Asmanex® drug product (200 microgram strength). The respirable agglomerate formulations were made according to Example 1. Thus, Lot #11015A-7-1 is the "mono"; Lot #11015A-7-5 is the "combo" formulated with indacaterol; and Lot #11015A-7-6 is the "trombo" (or triple combination) formulated with indacaterol and glycopyrrolate.

Figure 6:
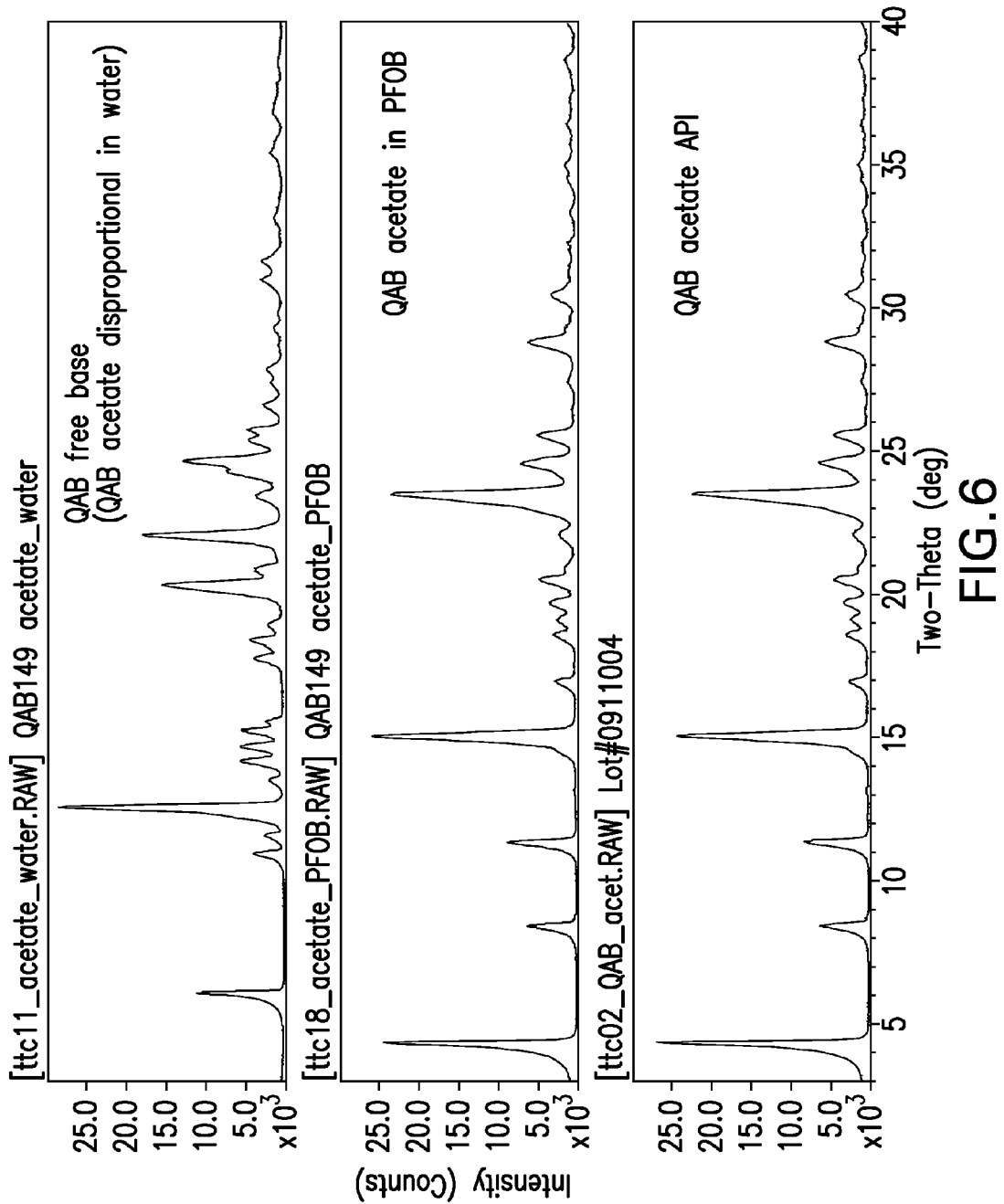

FIG. 6 illustrates three X-ray powder diffraction patterns for indacaterol drug substance as indacaterol free base in water (upper curve); as indacaterol acetate dispersed in PFOB (middle curve); and neat indacaterol acetate.

Figure 7:
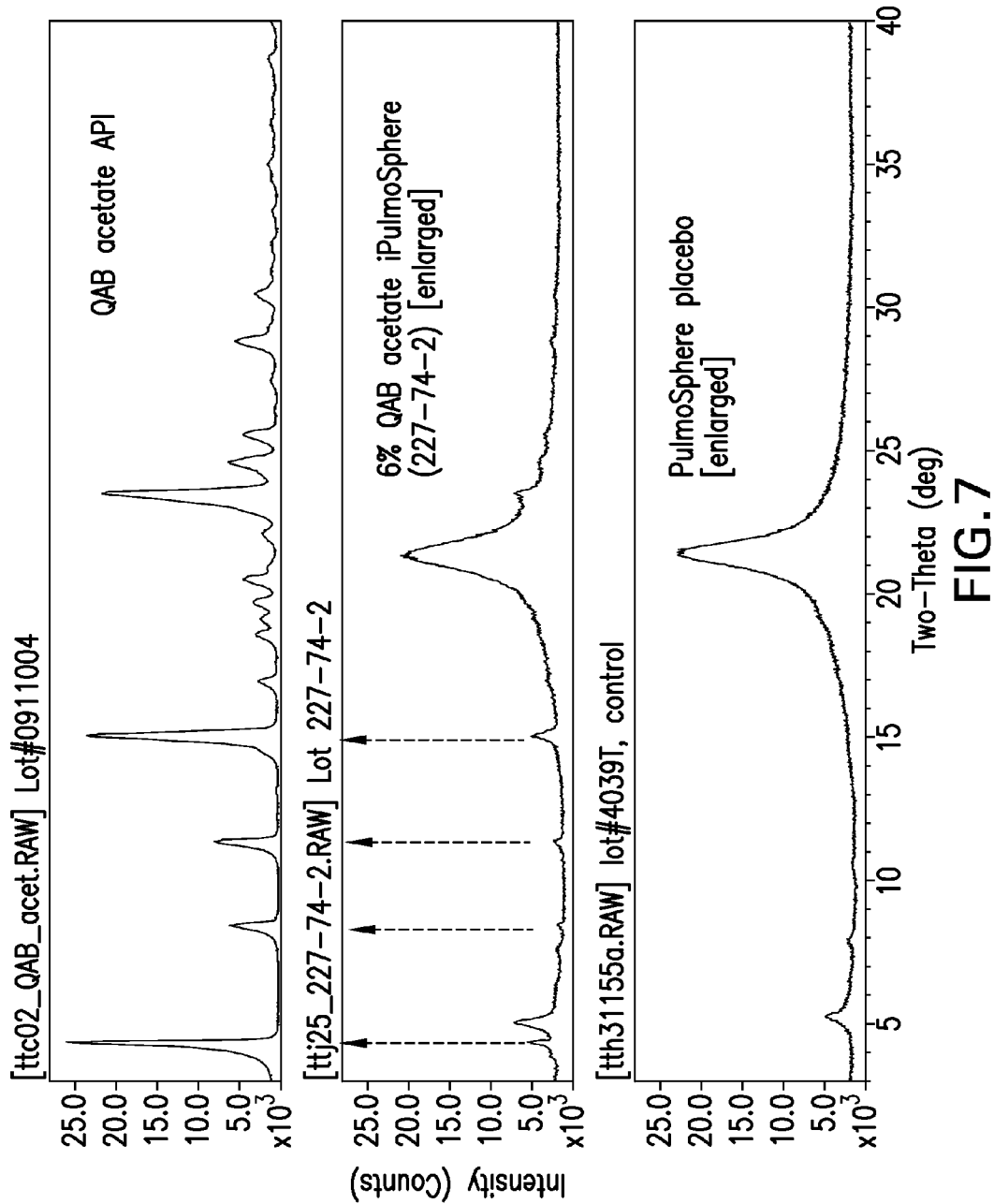

FIG. 7 illustrates X-ray powder diffraction patterns for indacaterol acetate formulated as dry powder respirable agglomerates (middle curve) in accordance with Example(s) 1—Lot 227-74-2. Also shown are the corresponding diffraction patterns for the near drug substance (upper curve) and the PulmoSphere placebo (lower curve). The diffraction pattern for the 6% QAB acetate formulation contains peaks characteristic of crystalline QAB acetate. No evidence of QAB free base is observed. These results confirm that the physical form of indacaterol acetate is maintained through the manufacturing process to prepare the respirable agglomerates.

DETAILED DESCRIPTION OF THE INVENTION

Embodiments of the present invention comprise a bulk powder composition comprising carrier particles associated with one, two, three or more micronized drugs or APIs forming stable respirable agglomerates suitable for pulmonary delivery, especially from an active or passive dry powder inhaler device. Embodiments of the present invention comprise a process to create the respirable agglomerates. Thus, in some embodiments, a dry powder comprising respirable agglomerates is achieved by creating a small and/or porous carrier particle, using a spray-drying process, then preparing a suspension of the desired drug or drugs and small carrier particle in an anti-solvent (e.g., perfluorooctyl bromide). The anti-solvent is then removed in a solvent removal step, such as by spray-drying, yielding the stable dry powder comprising respirable agglomerates.

Embodiments of the present invention comprise a dry powder formulation comprising respirable agglomerates, comprising an ordered mixture of carrier particles and one or more micronized drug particles. The physical form of the drug may be wholly or substantially crystalline or wholly or substantially amorphous. In embodiments of the present invention the drug is wholly or substantially crystalline, and amorphous content is minimal, such as less than 5%. In embodiments of the present invention the drug is wholly or substantially amorphous, and crystalline content is minimal, such as less than 0.1%. In embodiments of the invention the carrier particles have an MMD less than 10 microns, such as less than 5 microns, or less than 3 microns. In embodiments of the invention the drug particles have a mass median diameter (MMD) less than 3 microns, such as less than 2 microns, or less than 1.5 microns. In embodiments of the invention the respirable agglomerates comprise a size range substantially as that of the carrier particles.

Carrier Particle

The carrier particles comprise porous and/or perforated microstructures. In some embodiments the carrier particles comprise one or more of a rugous, a wrinkled and/or a raisin-like surface morphology. In embodiments of the present invention, the carrier particles comprise a sponge-like porous particle structure. In some embodiments the carrier particles are small, and comprise a geometric diameter of less than about 10 microns, such as less than 5 microns or less than 3 microns. In some embodiments the carrier particles comprise a geometric diameter of about 2 to 3 microns. In some embodiments a bulk, or dry, powder comprising the carrier particles has a tapped density of less than 0.5 g/cm$^3$, such as less than 0.2 g/cm$^3$ of less than 0.1 g/cm$^3$. In some embodiments, the carrier particles comprise combinations of these characteristics or attributes.

A porous particle morphology aids in making the agglomerate particles aerodynamic, and in facilitating dispersion of the powder agglomerates from a dry powder inhaler. The porous nature of the particles may also be important in achieving a strong adhesion with the micronized drug particles via interlocking forces between particles. A mass median diameter of the porous carrier particles is between 1 and 10 microns, such as between 1 and 5 microns or between 2 and 3 microns. Such small MMDs confers upon the small porous carrier particles a high surface to volume ratio, facilitating strong adhesion with the micronized drug particles. In embodiments of the invention, the carrier particles and drug particles substantially adhere during the powder manufacturing process. In embodiments of the invention, the carrier particles and drug particles substantially adhere during the powder manufacturing process and the process of filling the powder into unit doses. In embodiments of the invention, the carrier particles and drug particles substantially adhere during the powder making process and the process of filling the powder into unit doses, and during dispensing of the powder from an inhaler device.

In some embodiments of the invention, a tapped density of the small porous particles is less than about 0.5 g/cm$^3$, such as less than about 0.4 g/cm$^3$, or less than about 0.3 g/cm$^3$ or less than about 0.2 g/cm$^3$, or less than about 0.1 g/cm$^3$, or less than about 0.05 g/cm$^3$. In some embodiments of the invention, a tapped density of the small porous particles is between about 0.03-0.5 g/cm$^3$, with tapped densities less than about 0.3 g/cm$^3$ or less than about 0.1 g/cm$^3$ often preferred. The tapped density is a reasonable approximation of the particle density, typically being about 20% less than particle density.

In some embodiments of the present invention a MMAD of the small porous carrier particles is between 1 and 5 microns, such as between 1 and 4 microns, or 2 and 4 microns. In some embodiments the carrier particles have MMAD values between 2 and 4 microns or between 2 and 3 microns.

In some embodiments the porous carrier particles comprise one or more excipients. Particularly preferred are excipients with a history of use in pharmaceutical aerosols. Suitable excipients comprise carbohydrates, for example lactose, glucose, mannitol, phospholipids, for example, dipalmitoylphosphatidylcholine (DPPC), and distearoylphosphatidylcholine (DSPC), and hydrophobic amino acids or peptides, for example, leucine or trileucine. In some embodiments the excipients are those that enable the desired porous particle morphology.

In some embodiments, the small porous carrier particles of the present invention contain a pharmaceutically acceptable hydrophobic excipient.

In some embodiments, the hydrophobic excipient facilitates development of a rugous particle morphology. This means the particle morphology is wrinkled and creased rather than smooth. This means the interior and/or the exterior surface of the inhalable medicament particles are at least in part rugous. This rugosity is useful for providing dose consistency and drug targeting by improving powder fluidization and dispersibility. Increases in particle rugosity result in decreases in inter-particle cohesive forces as a result of an inability of the particles to approach to within van der Waals contact. The decreases in cohesive forces are sufficient to dramatically improve powder fluidization and dispersion in ensembles of rugous particles, and in the respirable agglomerates comprising rugous carrier particles as well.

The rugosity of the small porous carrier particles may be increased by using a pore-forming agent, such as perflubron, during their manufacture, or by controlling the formulation and/or process to produce rugous particles.

In some embodiments the porous carrier particles of the dry powder formulation of the invention suitably have a rugosity of greater than 1.5, for example from 1.5 to 20, 3 to 15, or 5 to 10.

The hydrophobic excipient may take various forms that will depend at least to some extent on the composition and intended use of the dry powder formulation. Suitable pharmaceutically acceptable hydrophobic excipients may, in general, be selected from the group consisting of long-chain phospholipids, hydrophobic amino acids and peptides, and long chain fatty acid soaps.

Phospholipids from both natural and synthetic sources may be used in varying amounts. When phospholipids are present, the amount is typically sufficient to provide a porous coating matrix of phospholipids. If present, phospholipid content generally ranges from about 40-99% w/w of the medicament, for example 70% to 90% w/w of the medicament. The high percentage of excipient is also driven by the high potency and therefore typically small doses of the active agents. The excipients also serve as bulking agents in the formulation, enabling effective delivery of low dose therapeutics.

Generally compatible phospholipids comprise those having a gel to liquid crystal phase transition greater than about 40° C., such as greater than 60° C., or greater than about 80° C. The incorporated phospholipids may be relatively long chain (e.g., $C_{16}$-$C_{22}$) saturated phospholipids. Exemplary phospholipids useful in the disclosed stabilized preparations include, but are not limited to, phosphatidylcholines, such as dipalmitoylphosphatidylcholine (DPPC), distearoylphosphatidylcholine (DSPC), and hydrogenated egg or soy phosphatidylcholines (e.g., E-100-3, S-100-3, available from Lipoid KG, Ludwigshafen, Germany). Natural phospholipids are preferably hydrogenated, with a low iodine value (<10).

The phospholipids may optionally be combined with cholesterol to modify the fluidity of the phospholipid acyl chains.

The long-chain phospholipids may optionally be combined with a divalent metal ion (e.g., calcium, magnesium). Such a divalent metal ion acts to decrease headgroup hydration, thereby increasing the phospholipid gel to liquid crystal phase transition, and the wettability of the powders on lung lining fluid. The molar ratio of polyvalent cation to phospholipid may be at least about 0.05:1, such as about 0.05:1 to 0.5:1. In one or more embodiments, a molar ratio of polyvalent cation:phospholipid is 0.5:1. While not intending to be bound by theory, it is believed that the divalent metal ion binds to the phosphate groups on the zwitterionic phosphatidylcholine headgroup, displacing water molecules in the process. Molar ratios of metal ion to phospholipid in excess of 0.5 may result in free metal ion not bound to the phosphate groups. This can significantly increase the hygroscopicity of the resulting dry powder, and is not preferred. When the polyvalent metal ion is calcium, it may be in the form of calcium chloride. Although metal ions, such, as calcium, are often included with phospholipids, none is required, and their use can be problematic when other ions are present in the formulation (e.g., phosphate, which may precipitate the calcium ions as calcium phosphate). When compatibility issues occur, there may be benefit in using $Mg^{++}$ salts, as they typically have $K_{sp}$ values which are three to four orders of magnitude higher than $Ca^{++}$ salts.

The hydrophobic excipient may also comprise long chain fatty acid soaps. The alkyl chain length is generally 14-22 carbons in length with saturated alkyl chains preferred. The fatty acid soaps may utilize monovalent (e.g., $Na^+$, $K^+$) or divalent counterions (e.g., $Ca^{++}$, $Mg^{++}$). Particularly preferred fatty acid soaps are sodium stearate and magnesium stearate. The solubility of fatty acid soaps may be increased above the Krafft point. Potassium salts of fatty acids generally have the lowest Krafft point temperature and greater aqueous solubility at a given temperature. Calcium salts are expected to have the lowest solubility. The hydrophobic fatty acid soaps provide a wax-like coating on the particles. The proposed loadings in the spray-dried particles are similar to the phospholipids detailed previously.

The hydrophobic excipient may also comprise hydrophobic amino acids, peptides, or proteins. Particularly preferred are the amino acid leucine, and its oligomers dileucine and trileucine. Proteins, such as human serum albumin are also contemplated. Trileucine is particularly preferred, as its solubility profile and other physicochemical properties (e.g., surface activity, log P) facilitate creation of core-shell particles, where trileucine controls the surface properties and morphology of the resulting particles.

In embodiments of the present invention, the carrier particles comprise porous and/or perforated particles which are engineered using the emulsion-based PulmoSphere dry powder manufacturing technology, as more fully described in U.S. Pat. No. 6,565,885, U.S. Pat. No. 7,871,598 and U.S. Pat. No. 7,442,388. In particular embodiments, a method of preparing perforated microstructures for pharmaceutical applications comprises spray-drying a feedstock comprising an agent (API or drug), a surfactant (e.g., a phospholipid) and a blowing agent. The resulting perforated microstructures comprise the agent and the surfactant and are known as PulmoSphere particles.

In embodiments herein, the carrier particles are prepared as spray-dried PulmoSphere particles as described herein and/or in the above-referenced US patents and/or applications, but without a drug or API. In some embodiments herein, the carrier particles are prepared as spray-dried PulmoSphere particles consisting essentially of one or more phospholipids and a multivalent metal cation. In some embodiments herein, the carrier particles are prepared as spray-dried PulmoSphere particles consisting essentially of DSPC and calcium chloride, or DSPC and magnesium chloride.

In some embodiments the multivalent metal cation comprises a divalent cation, including calcium, magnesium, and the like. The mutivalent cation, in some embodiments, is present in an amount effective to increase the $T_m$ of the phospholipid such that the particulate composition exhibits a $T_m$ which is greater than its storage temperature $T_s$ by at least 20° C., preferably at least 40° C. If present, a molar ratio of multivalent cation to phospholipid may be at least 0.05, such as 0.05-2.0, or 0.25-1.0. In some embodiments, there is a molar ratio of multivalent cation:phospholipid of about 0.50. In some embodiments, the polyvalent cation comprises calcium, which may be provided as calcium chloride.

By control of the formulation and process, it is possible for the surface of the carrier particles to be comprised primarily of the hydrophobic excipient. Surface concentrations may be greater than 70%, such as greater than 75% or 80% or 85%. In some embodiments the surface is comprised of greater than 90% hydrophobic excipient, or greater than 95% or 98% or 99% hydrophobic excipient.

Optionally a drug or drugs (one or more APIs) may be incorporated directly with the carrier particles, in addition to the one or more micronized drugs associated with the carrier particles to form the respirable agglomerates. Such optional drug-containing carrier particles may be prepared in accordance with the teachings of U.S. Pat. Nos. 6,565,885, 7,871,598 and 7,442,388, for example.

Drug Particle

Embodiments of the present invention comprise a dry powder composition comprising small carrier particles associated with one, two, three or more drugs (also referred to herein as API, or active agent) wherein an ordered mixture between the micronized drug or drugs and the small carrier particle results, such that the micronized drug or drugs adhere to the small carrier particles forming a stable respirable agglomerate.

It is important that the drug particles be fine enough to adhere to the carrier particles. Accordingly, in some embodiments the drug particles and the small porous carrier particles are each sized such that adherence is mediated by van der Waals forces. In some embodiments the drug particles are much smaller than the small porous carrier particles such that adherence is mediated by van der Waals forces.

In embodiments of the invention, the active drug ingredient(s) is/are micronized. An MMD or an ×50 (particle size distribution wherein 50% of the particles are sized smaller) of the micronized active ingredients should be less than about 3 micron (μm), preferably less than about 2 μm, or 1 μm. In embodiments of the invention, an ×50 is about 0.1-3 μm. An ×90 (particle size distribution wherein 90% of the particles are sized smaller) should be less than 7 μm, preferably less than 5 μm, or 3 μm. As well, the MMAD of the respirable agglomerates will become increasingly influenced by the size of the drug crystals for particles with an ×50 greater than about 2 μm.

If micronized, the drug particles may be prepared by either top-down or bottom-up manufacturing processes. Top-down manufacturing processes include jet milling, ball milling, media milling, and high pressure homogenization. Bottom-up processes include: spray-drying, spray freeze-drying, supercritical fluid technologies (rapid expansion and anti-solvent), templating and microfabrication, lithography, and other particle precipitation techniques (e.g., spinodal decomposition), for example in the presence of ultrasonic energy to ensure crystallization of the drug. Note that the term micronized is intended to encompass any and all processes, whether physical, chemical, mechanical or otherwise, for providing a sufficiently sized and/or shaped drug particle.

In embodiments of the invention the drug particles comprise nano-sized particles with mass median diameters less than 1000 nm, or less than 200 or less than 100 nm. For embodiments comprising nanoparticles, the ×90 may be less than 1000 nm. Drug particles within these size ranges enable their association with the porous particles, to afford the desired respirability, and drug delivery and drug efficacy of the dry powder comprising respirable agglomerates.

The active agent(s) of the dry powder of the present invention can be any active pharmaceutical ingredient that is useful for treating diseases or conditions, such as lung and/or airway diseases or conditions, for example obstructive or inflammatory airways diseases, particularly asthma and/or COPD, pulmonary arterial hypertension (PAH), idiopathic pulmonary fibrosis (IPF), and cystic fibrosis (CF). The active agent(s) of the dry powder of the present invention can also be any pharmaceutical ingredient that is useful for treating systemic diseases or conditions following administration as a dry powder aerosol to the lungs and subsequent absorption of the active agent(s) to the systemic circulation. The active ingredient(s) may be selected, for example, from bronchodilators, anti-inflammatories, and mixtures thereof, especially $\beta_2$-agonists, muscarinic antagonists, steroids, dual $\beta_2$-agonist-muscarinic antagonists, and nonsteroidal anti-inflammatory agents (e.g., PDE4 inhibitors, $A_{2A}$ agonists, cytokine inhibitors, chemokine antagonists, p38 MAP Kinase inhibitors, PI3K inhibitors, PPAR agonists) and mixtures thereof.

Suitable active agents include $\beta_2$-agonists. Suitable $\beta_2$-agonists include arformoterol (e.g., tartrate), albuterol/salbutamol (e.g., racemate or single enantiomer such as the R-enantiomer, or salt thereof especially sulfate), AZD3199, bambuterol, BI-171800, bitolterol (e.g., mesylate), carmoterol, clenbuterol, etanterol, fenoterol (e.g., racemate or single enantiomer such as the R-enantiomer, or salt thereof especially hydrobromide), flerbuterol, formoterol (e.g., racemate or single diastereomer such as the R,R-diastereomer, or salt thereof especially fumarate or fumarate dihydrate), GSK-159802, GSK-597901, GSK-678007, indacaterol (e.g., racemate or single enantiomer such as the R-enantiomer, or salt thereof especially maleate, acetate or xinafoate), LAS100977, metaproterenol, milveterol (e.g., hydrochloride), naminterol, olodaterol (e.g., racemate or single enantiomer such as the R-enantiomer, or salt thereof especially hydrochloride), PF-610355, pirbuterol (e.g., acetate), procaterol, reproterol, salmefamol, salmeterol (e.g., racemate or single enantiomer such as the R-enantiomer, or salt thereof especially xinafoate), terbutaline (e.g., sulphate) and vilanterol (or a salt thereof especially trifenatate). In certain preferred embodiments the $\beta_2$-agonist is an ultra-long-acting $\beta_2$-agonist such as indacaterol, or potentially carmoterol, LAS-100977, milveterol, olodaterol, PF-610355 or vilanterol.

In some embodiments one of the active agents is indacaterol (i.e., (R)-5-[2-(5,6-diethyl-indan-2-ylamino)-1-hydroxyethyl]-8-hydroxy-1H-quinolin-2-one) or a salt thereof. This is a $\beta_2$-adrenoceptor agonist that has an especially long duration of action (i.e., over 24 hours) and a short onset of action (i.e., about 10 minutes). This compound is prepared by the processes described in International Patent Applications WO 2000/75114 and WO 2005/123684. It is capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids such as formic acid, acetic acid, propionic acid, butyric acid, benzoic acid, o-hydroxybenzoic acid, p-hydroxybenzoic acid, p-chlorobenzoic acid, diphenylacetic acid, triphenylacetic acid, 1-hydroxynaphthalene-2-carboxylic acid, 3-hydroxynaphthalene-2-carboxylic acid, aliphatic hydroxy acids such as lactic acid, citric acid, tartaric acid or malic acid, dicarboxylic acids such as fumaric acid, maleic acid or succinic acid, and sulfonic acids such as methanesulfonic acid or benzenesulfonic acid. These salts may be prepared from the compound by known salt-forming procedures. A preferred salt of (R)-5-[2-(5,6-diethyl-indan-2-ylamino)-1-hydroxyethyl]-8-hydroxy-1H-quinolin-2-one is the maleate salt. Another preferred salt is (R)-5-[2-(5,6-diethyl-indan-2-ylamino)-1-hydroxyethyl]-8-hydroxy-1H-quinolin-2-one acetate. Another preferred salt is (R)-5-[2-(5,6-diethyl-indan-2-ylamino)-1-hydroxyethyl]-8-hydroxy-1H-quinolin-2-one xinafoate. Other useful salts include the hydrogen succinate, fumarate, hippurate, mesylate, hydrogen sulphate, hydrogen tartrate, hydrogen chloride, hydrogen bromide, formate, esylate, tosylate, glycolate and hydrogen malonate salts, which, like the acetate and xinafoate salts, are disclosed in International Patent Application WO 2008/000839 together with methods of their respective preparation.

Suitable active agents comprise muscarinic antagonists or antimuscarinics. Suitable muscarinic antagonists include aclidinium (e.g., bromide), BEA-2108 (e.g., bromide), BEA-2180 (e.g., bromide), CHF-5407, darifenacin (e.g., bromide), darotropium (e.g., bromide), glycopyrrolate (e.g., racemate or single enantiomer, or salt thereof especially bromide), dexpirronium (e.g., bromide), iGSK-202405, GSK-203423, GSK-573719, GSK-656398, ipratropium (e.g., bromide), LAS35201, LAS186368, otilonium (e.g., bromide), oxitropium (e.g., bromide), oxybutynin, PF-3715455, PF-3635659, pirenzepine, revatropate (e.g., hydrobromide), solifenacin (e.g., succinate), SVT-40776, TD-4208, terodiline, tiotropium (e.g., bromide), tolterodine (e.g., tartrate), and trospium (e.g., chloride). In some embodiments the muscarinic antagonists is long-acting muscarinic antagonist such as darotropium bromide, glycopyrrolate or tiotropium bromide.

In some embodiments one of the active agents is a glycopyrronium salt. Glycopyrronium salts include glycopyrronium bromide, also known as glycopyrrolate, which is known to be an effective antimuscarinic agent. More specifically it inhibits acetyl choline binding to M3 muscarinic receptors thereby inhibiting bronchoconstriction. Glycopyrrolate is a quaternary ammonium salt. Suitable counter ions are pharmaceutically acceptable counter ions including, for example, fluoride, chloride, bromide, iodide, nitrate, sulfate, phosphate, formate, acetate, trifluoroacetate, propionate, butyrate, lactate, citrate, tartrate, malate, maleate, succinate, benzoate, p-chlorobenzoate, diphenyl-acetate or triphenylacetate, o-hydroxybenzoate, p-hydroxybenzoate, 1-hydroxynaphthalene-2-carboxylate, 3-hydroxynaphthalene-2-carboxylate, methanesulfonate and benzenesulfonate. Glycopyrrolate can be prepared using the procedures described in U.S. Pat. No. 2,956,062. It has two stereogenic centers and hence exists in four isomeric forms, namely (3R,2'R)-, (3S,2'R)-, (3R,2'S)- and (3S,2'S)-3-[(cyclopentyl-hydroxyphenyl-acetyl)oxy]-1,1-dimethylpyrrolidinium bromide, as described in U.S. Pat. No. 6,307,060 and U.S. Pat. No. 6,613,795. When the drug substance of the dry powder formulation is glycopyrrolate, it can be one or more of these isomeric forms, especially the 3S,2'R isomer, the 3R,2'R isomer or the 2S,3'R isomer, thus including single enantiomers, mixtures of diastereomers, or racemates, especially (3S,2'R/3R,2'S)-3-[(cyclopentyl-hydroxy-phenylacetyl)oxy]-1,1-dimethylpyrrolidinium bromide. R,R-glycopyrrolate is also known as dexpirronium.

In some embodiments, suitable active agents include bifunctional active agents such as dual $\beta_2$-agonists-muscarinic antagonists. Suitable dual $\beta_2$-agonists-muscarinic antagonists include GSK-961081 (e.g., succinate).

In some embodiments, suitable active agents include steroids, for example corticosteroids. Suitable steroids include budesonide, beclamethasone (e.g., dipropionate), butixocort (e.g., propionate), CHF5188, ciclesonide, dexamethasone, flunisolide, fluticasone (e.g., propionate or furoate), GSK-685698, GSK-870086, LAS40369, methyl prednisolone, mometasone (e.g., furoate), prednisolone, rofleponide, and triamcinolone (e.g., acetonide). In certain preferred embodiments the steroid is long-acting corticosteroids such as budesonide, ciclesonide, fluticasone or mometasone.

In some embodiments one of the active agents is mometasone (i.e., (11$\beta$, 16$\alpha$)-9,21-dichloro-17-[(2-furanylcarbonyl)oxy]-11-hydroxy-16-methylpregna-1,4-diene-3,20-dione, alternatively designated 9$\alpha$,21-dichloro-16$\alpha$-methyl-1,4-pregnadiene-11$\beta$,17$\alpha$-diol-3,20-dione 17-(2'-furoate)) or a salt thereof, for example mometasone furoate and mometasone furoate monohydrate. Mometasone furoate and its preparation are described in U.S. Pat. No. 4,472,393. Its use in the treatment of asthma is described in U.S. Pat. No. 5,889,015. Its use in the treatment of other respiratory diseases is described in U.S. Pat. No. 5,889,015, U.S. Pat. No. 6,057,307, U.S. Pat. No. 6,057,581, U.S. Pat. No. 6,677,322, U.S. Pat. No. 6,677,323 and U.S. Pat. No. 6,365,581.

Pharmaceutically acceptable esters, acetals, and salts of the above therapeutics are contemplated. The determination of the appropriate esters, acetals, or salt form is driven by the duration of action and tolerability/safety data. As well, API selection may be important from the standpoint of selecting therapeutics with the appropriate physical properties (e.g., solubility) to achieve the embodiments of the present invention.

Suitable PAH drugs include Notch 3 inhibitors, such as DAPT; vasodilators, such as serelaxin and sodium nitrite; IP receptor agonists, such as selexipag; activators of soluble guanylate cyclase, such as cinaciguat and riociguat; prostacyclin receptor antagonists, such as epoprostenol, iloprost, treprostinil and beraprost; phosphodiesterase type 5 inhibitors, such as sildenafil and tadalafil; endothelin receptor antagonists, such as bosentan, ambrisentan and sitaxentan; platelet derived growth factor receptor antagonists, such as imatinib (Gleevec); and calcium channel blockers, such as amlodipine, nifedipine and diltiazem. Suitable drugs to treat IPF include TGF-Beta inhibitors, such as pirfenidone and Interferon-gamma, low molecular weight heparin, and serelaxin.

Suitable drugs to treat CF include CFTR modulators, such as ivacaftor (VX-770), PTC-124, N-6022, VX-661 and VX-809; mucus alteration agents, such as Dornase alfa, sodium chloride and mannitol; and epthelial sodium channel inhibitors.

Useful antiinfectives include tobramycin, azithromycin, ciprofloxacin, levofloxacin, aztreonam, fosfomycin, vancomycin, amikacin, gentamicin and amphotericin B.

Fixed Dose Combinations

The dry powder composition, comprising respirable aggregates of the present invention can contain one, two, three, four or more therapeutically active agents that are useful for treating diseases and/or conditions, such as lung diseases, obstructive or inflammatory airways diseases, particularly asthma and COPD.

Some embodiments of the present invention comprise spray-dried particles comprising two active agents (double combinations).

Embodiments of the present invention comprise combinations such as those that contain a $\beta_2$-agonist and a corticosteroid. Exemplary embodiments of combinations are shown by the parentheticals: (carmoterol and budesonide), (formoterol and beclomethasone), (formoterol fumarate and budesonide), (formoterol fumarate dihydrate and mometasone furoate), (formoterol fumarate and ciclesonide), (indacaterol maleate and mometasone furoate), (indacaterol acetate and mometasone furoate), (indacaterol xinafoate and mometasone furoate), (milveterol hydrochloride and fluticasone), (olodaterol hydrochloride and fluticasone furoate), (olodaterol hydrochloride and mometasone furoate), (salmeterol xinafoate and fluticasone propionate), (vilanterol trifenatate and fluticasone furoate), and (vilanterol trifenatate and mometasone furoate); a $\beta_2$-agonist and a muscarinic antagonist, for example (formoterol and aclidinium bromide), (indacaterol and darotropium), (indacaterol maleate and glycopyrrolate); (indacaterol acetate and glycopyrrolate); (indacaterol xinafoate and glycopyrrolate); (indacaterol maleate and GSK573719), (milveterol hydrochloride and glycopyrrolate), (milveterol hydrochloride and tiotropium bromide), olodaterol hydrochloride and glycopyrrolate), (olodaterol hydrochloride and tiotropium bromide), (salmeterol xinafoate and tiotropium bromide), (vilanterol trifenatate and darotropium), (vilanterol trifenatate and glycopyrrolate), (vilanterol trifenatate and GSK573719), and (vilanterol trifenatate and tiotropium bromide); and a muscarinic antagonist and a corticosteroid, for example (glycopyrrolate and mometasone furoate), and (glycopyrrolate and ciclesonide); or a dual $\beta_2$-agonist-muscarinic antagonist and a corticosteroid, for example (GSK-961081 succinate and mometasone furoate), (GSK-961081 succinate and mometasone furoate monohydrate), and (GSK-961081 succinate and ciclesonide). It should be noted that virtually any combinations are possible, including combinations between actives described in parentheticals, and with others.

Some embodiments of the present invention comprise spray-dried particles comprising three active agents (triple combinations).

Embodiments of the present invention comprise triple combinations such as those that contain a $\beta_2$-agonist, a muscarinic antagonist and a corticosteroid, for example (salmeterol xinafoate, fluticasone propionate and tiotropium bromide), (indacaterol maleate, mometasone furoate and glycopyrrolate), (indacaterol acetate, mometasone furoate and glycopyrrolate), (indacaterol xinafoate, mometasone furoate and glycopyrrolate), (vilanterol trifenatate, umeclidinium bromide, and fluticasone furoate), (olodaterol hydrochloride, tiotropium bromide, and mometasone furoate), (olodaterol hydrochloride and tiotropium bromide, and ciclesonide), and (indacaterol acetate, tiotropium bromide, and mometasone furoate).

Respirable Agglomerates

In embodiments of the present invention, the bulk dry powder comprising respirable agglomerates is engineered to be storage stable for extended periods of time, to readily and efficiently dispense from both passive and active, single dose or multi-dose, dry powder inhalers, and to provide efficacious delivery to the target region of the lung or pulmonary system.

In embodiments of the present invention, the bulk dry powder comprising respirable agglomerates is engineered to reduce interagglomerate forces, such as by the inclusion of pores or asperities in the surface of the carrier particles, and/or by the enrichment of a hydrophobic excipient at the surface of the carrier particles.

In embodiments of the invention, the respirable agglomerates of drug and carrier comprises a mass median diameter (MMD) less than 10 microns, such as a MMD between about 1 and 5 microns, with an exemplary embodiment having a MMD of about 2 to 3. In embodiments of the invention the mass median aerodynamic (MMAD) diameter of the powder agglomerate is between about 1 and 5 microns, with an exemplary embodiment having a MMAD of about 2 to 4 microns. In embodiments of the invention, deposition of the respirable agglomerates in the idealized Alberta mouth-throat is less than 50%, such as less than 35% or deposition less than 20%. Hence, embodiments of the invention provide delivery of a respirable fraction of drug or drugs to the targeted regions of the lung of greater than about 40%, such as greater than 50% or 60% or 70% or 80%.

In embodiments of the present invention, the dry powder comprising respirable agglomerates has a tapped density of less than about 0.5 g/cm$^3$, such as less than 0.3 g/cm$^3$ or less than 0.1 g/cm$^3$.

Embodiments of dry powder formulations of the present invention may comprise 0.1% to 30% w/w of active ingredient(s), such as about 0.5% to 20% w/w, or 5% to 15% w/w.

Embodiments of the present invention are useful for engineering particles comprising active ingredients with a low powder mass per dose, such as less than about 50 milligrams, or less than 15 or 5 or 2 or 1 milligrams per dose.

Embodiments of the present invention are useful for engineering respirable agglomerate particles comprising highly potent active ingredients with a nominal dose of active drug of about 100 nanograms (ng) to 5 mg.

Embodiments of the present invention are useful for engineering spray-dried particles comprising respirable agglomerates comprising one or more potent active ingredients wherein the one or more active ingredients is characterized by a limited solubility in the feedstock to be spray-dried, and wherein the process and formulation maintains crystallinity of the active in the resultant dried drug product.

In some embodiments the respirable agglomerates of the dry powder formulation of the invention suitably have a rugosity of greater than 1.5, for example from 1.5 to 20, 3 to 15, or 5 to 10.

In some embodiments the dry powder formulation comprising respirable agglomerates of the invention comprise a fine particle fraction, expressed as a percentage of the nominal dose <3.3 µm ($FPF_{<3.3\ \mu m}$) of greater than about 40%, such as greater than about 50%, or greater than about 60%.

In some embodiments of the present invention the dry powder formulation comprising respirable agglomerates of the invention comprise a fine particle fraction, expressed as a percentage of the nominal dose less than 4.7 (i.e., $FPF_{<4.7\ \mu m}$) of greater than about 50%, such as greater than about 60%, or greater than about 70%.

In some embodiments of the present invention the dry powder formulation comprising respirable agglomerates of the invention comprise a fine particle fraction, expressed as a percentage of the nominal dose on stage 4 to filter ($FPF_{S4-F}$) of at least 40% of a nominal dose, such as greater than 50% or 60% of a nominal dose.

In some embodiments of the dry powder formulation of the invention comprising respirable agglomerates, lung deposition is at least 40-80% of the nominal dose. In some embodiments, inter-patient variability in lung deposition is minimized, such as less than about 20% or 10%.

Embodiments of dry powder formulations comprising respirable agglomerates of the present invention provide for delivery of the respirable agglomerates from a passive dry powder inhaler in a manner which is substantially independent of the patient's peak inspiratory flow rate (PIF).

Embodiments of the present invention yield respirable agglomerate particles exhibiting a good correlation in the aerodynamic particle size distributions of an active agent when it is formulated as a mono product, or in fixed dose combinations with other active agents. The equivalence in the APSD is assessed by comparison of various stage groupings. Embodiments of the present invention yield a variability in the large particle dose (stage 0 to stage 2) within 25%, preferably within 15% or 10% for the various mono and combo products. In some embodiments variation in the fine particle dose (stage 3 to filter) is within 15%, preferably within 10% or 5%. Additionally or alternatively, in some embodiments the variation in the very fine particle fraction (stage 4 to filter) is within 15%, preferably within 10% or 5%.

The engineered powders of the present invention provide excellent uniformity in the emitted dose or emitted powder mass from measurement to measurement. In some embodiments, the variability is within the FDA Draft Guidance which stipulates that 90% of the measurements should be within a 20% deviation from the label claim with none outside of 25%. In some embodiments 90% of the measurements are within a 15% deviation from the label claim, or within 10% of the label claim.

In one or more embodiments of the dry powder formulation comprising respirable agglomerates of the present invention, the dry powder formulation may additionally include additives such as those which may further enhance the stability, biocompatibility or patient acceptance of the formulation. For example, various salts, buffers, chelators, bulking agents, common ions, glass forming excipients, and taste masking agents are contemplated. Such optional agents may be incorporated in the bulk dry powder, or directly with the carrier particles.

In some embodiments, the dry powder formulation of the present invention contains a pharmaceutically acceptable excipient, for example a hydrophobic excipient.

Process

In some embodiments, the carrier particles are formed in a process comprising the step of spray-drying an emulsion-based feedstock comprising submicron droplets of a perfluorinated liquid, stabilized by a monolayer of a long-chain phospholipid and a multivalent metal ion, such as calcium chloride. During spray-drying the slow diffusing emulsion droplets are concentrated at the receding surface of the evaporating atomized droplet. As the drying process continues and the continuous water phase evaporates, the phospholipid forms a skin on the surface of the particle. Eventually the perfluorinated liquid outgases leaving behind dry powder particles with a sponge-like particle morphology. The carrier powder particles are often porous, and typically have a tapped density less than 0.5 g/cm$^3$, more often on the order of 0.1 g/cm$^3$ or less. The tapped density can be controlled via control of the volume fraction of perfluorinated oil in the emulsion. The complex morphology of interconnected pores provides a unique template for fine micronized or nanonized drug crystals to adhere and form an interlocking structure within the pores.

In some embodiments, the porous carrier particles may be formed by a process comprising spray-drying a solution comprising hydrophobic amino acids or peptides, such as leucine, or trileucine or polyols such as mannitol. For leucine and mannitol, the spray-drying process results in primarily crystalline excipient. Such carrier particles may be spray-dried to have a corrugated, or rugous particle morphology. Combinations of leucine or trileucine with a carbohydrate (e.g., sucrose, trehalose, mannitol) is also contemplated. In this case the surface of the corrugated particles will be enriched in the hydrophobic amino acid.

In some embodiments of the present invention the dry powder comprising respirable agglomerate particles are made by a process which has as an initial step dispersing the carrier particles in an anti-solvent, and then subsequently removing the liquid to create the dry powder agglomerates. Particularly preferred anti-solvents are perfluorinated liquids (e.g., perfluorooctyl bromide, perfluorodecalin), or hydrofluoroalkanes (e.g., perfluorooctyl ethane, HFA-134a, HFA-227ea). Owing to its large body of preclinical and clinical safety data, perfluorooctyl bromide (PFOB) is preferred.

The solids loading of drug and carrier particles in the anti-solvent is generally greater than about 50 g/L, often greater than 100 g/L or 150 g/L, and may be greater than 200 g/L or more. The solids loading will be dictated by the rheological properties and stability of the liquid feedstock and the density of carrier particles. The suspension must be stable enough and sufficiently flowable in tubing so as to quantitatively feed a uniform composition of material to the spray-drier over time.

The ordered mixture of drug and carrier is formed in the anti-solvent, as a result of the desire of the drug substance to remove contact with the anti-solvent. This is analogous to how foods do not stick to the surface of a Teflon® frying pan.

The anti-solvent is then removed via a solvent removal or drying process with spray-drying one of the preferred solvent removal process embodiments. In embodiments of the present invention, the liquid dispersion medium has a vapor pressure/boiling point that enables effective removal of the liquid during the applicable solvent removal (e.g., spray-drying) process. It is important that the drug or drugs have very low solubility in the anti-solvent. This aids in maintaining the crystallinity of the drug substance and prevention of the formation of amorphous material during spray drying. In some embodiments, the drug or drugs comprise a crystallinity of at least about 95%, such as 99%. In some embodiments, the initial crystallinity of the drug is maintained during the manufacture of the respirable agglomerates.

The presence of amorphous drug domains in crystalline micronized drugs for inhalation is generally thought to be undesirable. Amorphous domains are thermodynamically unstable, and may convert to a stable crystalline polymorph over time. The recrystallization process often results in coarsening of the micronized drug particles and decreased aerosol performance. The higher energy amorphous domains may also exhibit greater solubility, more rapid dissolution, and decreased chemical stability as compared to the crystalline drug. Embodiments of the present invention minimize the formation of amorphous domains in the active ingredient during spray-drying, by decreasing the percentage dissolved active ingredient in the liquid feedstock to be spray-dried. Embodiments of the present invention minimize exposure of the micronized drugs to water during the particle formation process, thus minimizing the possibility of any drug dissolving in aqueous media and subsequently being dried in a less stable amorphous state.

In some embodiments, the respirable agglomerates comprise, for example, a carrier particle and indacaterol acetate. Indacaterol acetate exhibits poor physical stability in water, rapidly disproportionating to form indacaterol free base and acetic acid. As such, the drug substance is not suitable for spray-drying processes which involve processing the drug in water. Formulation of indacaterol acetate as a suspension in an oil-in-water emulsion results in rapid disproportionation of the drug during the spray-drying process. With the non-aqueous component of embodiments of the process of the present invention, the physical stability of the drug substance can be maintained.

Moreover, owing to the short timescales of the spray-drying process (i.e., milliseconds), most drugs which are dissolved in an aqueous or non-aqueous feedstock, will be present as an amorphous solid in the spray-dried drug product. For some drugs formulation as an amorphous solid may result in increased degradation that may be unacceptable on storage. Hence, in some embodiments, the dry powder comprising respirable agglomerates, and process, of the present invention maintains the crystallinity of the drug substance through the manufacturing process and during storage for an extended period by preventing dissolution of drug(s) in the liquid to be spray-dried.

Alternatively, or additionally the respirable agglomerates may be formed in hydrofluoroalkane propellants under high pressure. The fluorocarbon may then be removed by vaporization at lower pressure without the need for a dedicated solvent removal step.

Unit Dosage Forms

Embodiments of the present invention provide a unit dosage form, comprising a container containing a dry powder formulation comprising the respirable agglomerates of the present invention.

In one embodiment, the present invention is directed to a unit dosage form, comprising a container containing a dry powder formulation comprising respirable agglomerates comprising about 0.5-3% w/w indacaterol acetate, about 0.5-3% w/w mometasone furoate, about 0.5-3% w/w glycopyrronium bromide, and about 91-99% small porous carrier particles comprising about a 2:1 molar ratio of DSPC:$CaCl_2$.

In one embodiment, the present invention is directed to a unit dosage form, comprising a container containing a dry powder formulation comprising respirable agglomerates comprising about 0.5-3% w/w indacaterol acetate and about 0.5-3% % w/w mometasone furoate, and about 94-99% small porous carrier particles comprising a 2:1 molar ratio of DSPC:$CaCl_2$.

In one embodiment, the present invention is directed to a unit dosage form, comprising a container containing a dry powder formulation comprising respirable agglomerates comprising about 0.5-3% w/w indacaterol acetate and about 0.5-3% % w/w glycopyrronium bromide, and about 94-99% small porous carrier particles comprising a 2:1 molar ratio of DSPC:$CaCl_2$.

Examples of containers include, but are not limited to, capsules, blisters, or container closure systems made of metal, polymer (e.g., plastic, elastomer), or the like. For current marketed asthma/COPD therapeutics, the fill mass in the container may be in the range from about 0.5 mg to 10 mg, such as in the range from 1 mg to 4 mg. In some embodiments, the powder comprising the respirable agglomerates is loaded into foil blisters. In some embodiments, the powder comprising the respirable agglomerates is loaded into containers with a fill mass of between about 0.5 and 10 mg, such as 1.0 mg to 4.0 mg.

Delivery System

The present invention also provides a delivery system, comprising an inhaler and a dry powder formulation of the invention.

In some embodiments, the present invention is directed to a delivery system, comprising a dry powder inhaler and a dry powder formulation comprising the respirable agglomerates for inhalation that comprises containing a dry powder formulation comprising a dry powder formulation comprising respirable agglomerates comprising about 2.2% w/w indacaterol acetate, about 2.0% w/w mometasone furoate, about 2.4% w/w glycopyrronium bromide, and about 93.4% small porous carrier particles comprising a 2:1 molar ratio of DSPC:$CaCl_2$.

Suitable inhalers comprise dry powder inhalers (DPIs). Some such inhalers include unit dose inhalers, where the dry powder is stored in a capsule or blister, and the patient loads one or more of the capsules or blisters into the device prior to use. Other multi-dose dry powder inhalers include those where the dose is pre-packaged in foil-foil blisters, for example in a cartridge, strip or wheel. Other multi-dose dry powder inhalers include those where the bulk powder is packaged in a reservoir in the device.

Embodiments of dry powder inhalers comprise multi-dose dry powder inhalers such as the DISKUS™ (GSK, described in U.S. Pat. No. 6,536,427), DISKHALER™ (GSK, described in WO 97/25086), GEMINI™ (GSK, described in WO 05/14089), GYROHALER™ (Vectura, described in WO 05/37353), PROHALER™ (Valois, described in WO 03/77979) and TWISTHALER™ (Merck, described in WO 93/00123, WO 94/14492 and WO 97/30743) inhalers. A reservoir type multi-dose inhaler is the TURBOHALER™ (AstraZeneca) as described in EP 0258238 (Virtanen), CLICKHALER®, and NOVOLIZER® (Meda).

Embodiments of single dose dry powder inhalers comprise the AEROLIZER™ (Novartis, described in U.S. Pat. No. 3,991,761) and the device referred to sometimes herein as CONCEPT1 or BREEZHALER™ (Novartis, described in US Patent Application Publication 2007/0295332 (Ziegler et al.). Other suitable single-dose inhalers include those described in U.S. Pat. Nos. 8,069,851 and 7,559,325 both to Dunkley et al., and in US Patent Application Publication 2010/0108058 to Glusker et al.

Suitable active inhalers comprise pressurizable dry powder inhalers, as disclosed, for example in WO 96/09085, WO 00/072904, WO 00/021594 and WO 01/043530, and ASPI-RAIR™ (Vectura) inhalers. Other active devices may include those available from MicroDose Technologies Inc., such as the device described in US Patent Application Publication 2005/0183724, referred to sometimes herein as "Genie".

Use in Therapy

Embodiments of the present invention comprise a dry powder medicament formulation comprising respirable agglomerates comprising of two or more active ingredients that are useful for pulmonary administration, such as for treating diseases of the lungs and/or airways.

Embodiments of the present invention comprise a method for treating diseases or conditions of a patient or subject, such as diseases or conditions of the lungs and/or airways, the treatment which comprises administering to a patient (or subject) having a disease or condition an effective amount of any dry powder formulation herein comprising respirable agglomerates. Exemplary diseases or conditions include obstructive or inflammatory airways disease, such as obstructive pulmonary disease (COPD), asthma, idiopathic pulmonary fibrosis, bronchiectasis, and cystic fibrosis as well as lung diseases such as pulmonary arterial hypertension.

In one or more embodiments, a method of treatment comprises administering to a subject a dry powder formulation comprising respirable agglomerates comprising about 0.5-3% % w/w indacaterol acetate, about 0.5-3% w/w mometasone furoate, about 0.5-3% % w/w glycopyrronium bromide, and about 93.4% small porous carrier particles comprising a 2:1 molar ratio of DSPC:CaCl$_2$.

In one or more embodiments, a method of treatment comprises administering to a subject a dry powder formulation comprising respirable agglomerates comprising about 0.5-3% w/w indacaterol acetate and about 0.5-3% w/w mometasone furoate, and about 94-99% small porous carrier particles comprising a 2:1 molar ratio of DSPC:CaCl$_2$.

In one or more embodiments, a method of treatment comprises administering to a subject a dry powder formulation comprising respirable agglomerates comprising about 0.5-3% w/w indacaterol acetate and about 0.5-3% w/w glycopyrronium bromide, and about 94-99% small porous carrier particles comprising a 2:1 molar ratio of DSPC:CaCl$_2$.

The present invention also relates to the use of any dry powder formulation herein in the manufacture of a medicament for the treatment of treating diseases or conditions of a patient or subject, such as diseases or conditions of the lungs and/or airways.

The present invention also provides any dry powder formulation herein comprising respirable agglomerates for use in the treatment of diseases or conditions of a patient or subject, such as diseases or conditions of the lungs and/or airways.

Treatment of a disease in accordance with embodiments of the invention may be symptomatic or prophylactic treatment or both. Obstructive or inflammatory airways diseases include asthma of various types or genesis including both intrinsic (non-allergic) asthma and extrinsic (allergic) asthma. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma can be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, for example anti-inflammatory (e.g., corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g., between the hours of about 4 to 6 am, i.e., at a time normally substantially different from any previously administered symptomatic asthma therapy.

Other obstructive or inflammatory airways diseases and conditions include acute/adult respiratory distress syndrome (ARDS), chronic obstructive pulmonary or airways disease (COPD or COAD), including chronic bronchitis, or dyspnea associated therewith, emphysema, as well as exacerbation of airways hyperreactivity consequent to other drug therapy, in particular other inhaled drug therapy. Embodiments of a dry powder formulation comprising respirable agglomerates of the invention are also applicable to the treatment of bronchitis of whatever type or genesis including, e.g., acute, arachidic, catarrhal, croupus, chronic or phthinoid bronchitis. Further obstructive or inflammatory airways diseases to which embodiments of the invention are applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis. Also contemplated is bronchiectasis associated with cystic fibrosis, and non-CF bronchiectasis, pulmonary arterial hypertension, and idiopathic pulmonary fibrosis.

Embodiments of the dry powder formulation of the present invention comprising respirable agglomerates are especially useful for treating asthma, COPD or both.

Additional embodiments and features are set forth in part in the description that follows, and in part will become apparent to those skilled in the art upon examination of the specification or may be learned by the practice of the invention.

This invention is further illustrated by the following examples which should not be construed as limiting.

KEY TO ABBREVIATIONS USED IN THE EXAMPLES

The following abbreviations are used in the Examples:
API Active Pharmaceutical Ingredient
DSPC Distearoylphosphatidylcholine
PFOB Perfluorooctyl bromide
RSD Relative Standard Deviation
RP-HPLC Reverse phase high performance liquid chromatography

EXAMPLES

Example 1

Manufacture of Ordered Mixes Comprising Small Porous Particles and Micronized Drug This Example illustrates embodiments for the production of respirable agglomerates comprising small porous particle carrier particles and one, two and three micronized drug particles wherein the process comprises two discrete drying steps. In a first step, a plurality of small porous carrier particles are produced by a method comprising spray-drying an emulsion-based feedstock to produce small porous particles with a foam-like morphology. In this embodiment, the carrier particles comprise a 2:1 molar ratio of distearoyl-phosphatidylcholine to calcium chloride. Such particles are sometimes referred to as PulmoSphere™ particles, and are described herein. The PulmoSphere particles may optionally contain buffer and/or active agent. In a second process step in this embodiment, a suspension of the small porous (PulmoSphere™) particles (up to ≈20% w/v) is prepared in the anti-solvent perfluorooctyl bromide (PFOB). Micronized drug (up to ≈10% w/v) is then added to this suspension, forming a co-suspension. The co-suspension is then mixed with a high shear mixer. The drug crystals associate with the small porous carrier particles in the anti-solvent to form a suspension comprising an ordered mixture. The resulting suspension is then dried in a second solvent removal step, such as by spray-drying.

For some Examples, a laboratory scale process was utilized, which made use of Novartis' proprietary NSD scale dryer (Lot #227-74-1 and #227-74-2). Accordingly, a suspension of 5.5% w/v PulmoSphere vehicle particles (comprised of a 2:1 molar ratio of DSPC:CaCl$_2$ only) and 0.5% w/v micronized indacaterol maleate were dispersed in PFOB. The suspension was mixed under high shear for 2-3 minutes with an IKA T-25 high shear mixer at 4,000 RPM. The resulting feedstock was spray dried on the NSD spray dryer at an inlet temperature of 96° C., an outlet temperature of 83° C., an atomization gas flow of 19 SLPM, a drying gas flow of 700 SLPM, and a feed rate of 10 mL/min.

The Niro PSD-1 Scale Process.

For some Examples, a suspension comprising PulmoSphere carrier particles, comprised of a 2:1 molar ratio of DSPC:CaCl$_2$ only (10.0% w/v to 16.0% w/v), and one or more micronized active pharmaceutical ingredients (0.5% w/v to 7.3% w/v) was prepared in PFOB. The suspension was mixed under high shear for 1-5 minutes with an IKA T-25 high shear mixer at 4,000 RPM (in one instance a IKA T-50 high shear mixer was employed at 3,000 RPM for 3 minutes). A second feedstock was prepared comprising a fluorocarbon in water emulsion. The two feedstocks were spray blended on a Niro PSD-1 scale spray dryer with an inlet temperature of 140° C., and outlet temperature of 72-75° C., an atomization gas flow of 70 SLPM, a drying gas flow rate of 180-200 SLPM, a collector jacket temperature of 70° C., a feed rate for the PFOB-based feedstock of 14 to 31 g/min, and a feed rate for the emulsion-based feedstock of 47-90 g/min.

Table 1 provides the compositions for the respirable agglomerate lots prepared in the two processes described above. In Table 1, the abbreviated description independently describes the composition of the micronized crystalline drugs [in square brackets] and the carrier particles (in parentheses) in the final respirable agglomerate product. Note that empty parentheses denote a carrier particle as a PulmoSphere particle without any active or additional adjuncts. For example, Lot #227-74-1 contains 7.8% w/w micronized indacaterol maleate, with the balance being PulmoSphere vehicle particles (DSPC/CaCl$_2$). Lot #11015A-6-7 contains 2.6% w/w micronized indacaterol maleate, 2.0% w/w micronized mometasone furoate, with the small porous carrier particles comprising 2.6% w/w amorphous glycopyrronium bromide, 3.6% w/w sodium maleate buffer (pH 3.0), and 91.8% w/w DSPC/CaCl$_2$. Lot #11015A-7-6 is comprised of 2.2% w/w indacaterol acetate, 2.0% w/w mometasone furoate, 1.5% w/w glycopyrronium bromide, with the small porous carrier particles comprising 2.3% w/w sodium maleate buffer (pH 3.0) and 92.0% w/w DSPC/CaCl$_2$. Drug loadings given are for the entire salt.

TABLE 1

Compositions of respirable agglomerate lots

| Lot# | Abbreviated Description | Dryer |
|---|---|---|
| 227-74-1 | $\|QAB\text{-}AFA\|_{7.8\%}(\ )$ | NSD |
| 227-74-2 | $\|QAB\text{-}AKA\|_{7\%}(\ )$ | NSD |
| 11015A-6-7 | $\|QAB\text{-}AFA\|_{2.6\%}\|MF\|_{2.0\%}(NVA_{2.6\%}, NaMaleate^{pH=3}{}_{3.6\%})$ | PSD-1 |
| 11015A-7-1 | $\|MF\|_{2\%}(\ )$ | PSD-1 |
| 11015A-7-2 | $\|MF^*H2O\|_{2.1\%}(\ )$ | PSD-1 |
| 11015A-7-3 | $\|MF\|_{1\%}\|MF^*H2O\|_{1\%}(\ )$ | PSD-1 |
| 11015A-7-4 | $\|QAB\text{-}AKA\|_{2.2\%}\|MF\|_{2\%}(\ )$ | PSD-1 |
| 11015A-7-5 | $\|QAB\text{-}AKA\|_{2.2\%}\|MF\|_{2\%}(NaMaleate^{pH=3}{}_{2.3\%})$ | PSD-1 |
| 11015A-7-6 | $\|QAB\text{-}AKA\|_{2.2\%}\|MF\|_{2\%}\|NVA\|_{1.5\%}(NaMaleate^{pH=3}{}_{2.3\%})$ | PSD-1 |
| 11015A-7-7 | $\|MF\|_{25\%}(\ )$ | PSD-1 |
| 11015A-10-3 | $\|QAB\text{-}AKA\|_{2.2\%}\|MF\|_{2\%}\|NVA\|_{2.4\%}(\ )$ | PSD-1 |
| 11015A-10-4 | $\|QAB\text{-}AKA\|_{2.2\%}\|MF\|_{2\%}\|NVA\|_{2.4\%}(CaMalate^{pH=3.8}{}_{3.1\%})$ | PSD-1 |
| 11015A-10-5 | $\|QAB\text{-}AFA\|_{2.5\%}\|MF\|_{2\%}\|NVA\|_{2.4\%}(\ )$ | PSD-1 |
| 11015A-10-6 | $\|QAB\text{-}AFA\|_{2.5\%}\|MF\|_{2\%}\|NVA\|_{2.4\%}(CaMalate^{pH=3.8}{}_{3.1\%})$ | PSD-1 |

Drug mass percentages are expressed as the whole salt/solvate form.
Abbreviations: QAB-AFA (indacaterol maleate); QAB-AKA (indacaterol acetate); MF (mometasone furoate); MF*H2O (mometasone monohydrate); NVA (glycopyrronium bromide); NaMaleate (sodium maleate); Ca malate (calcium malate);

Example 2

SEM Photomicrograph of Respirable Agglomerates

Figure 1:
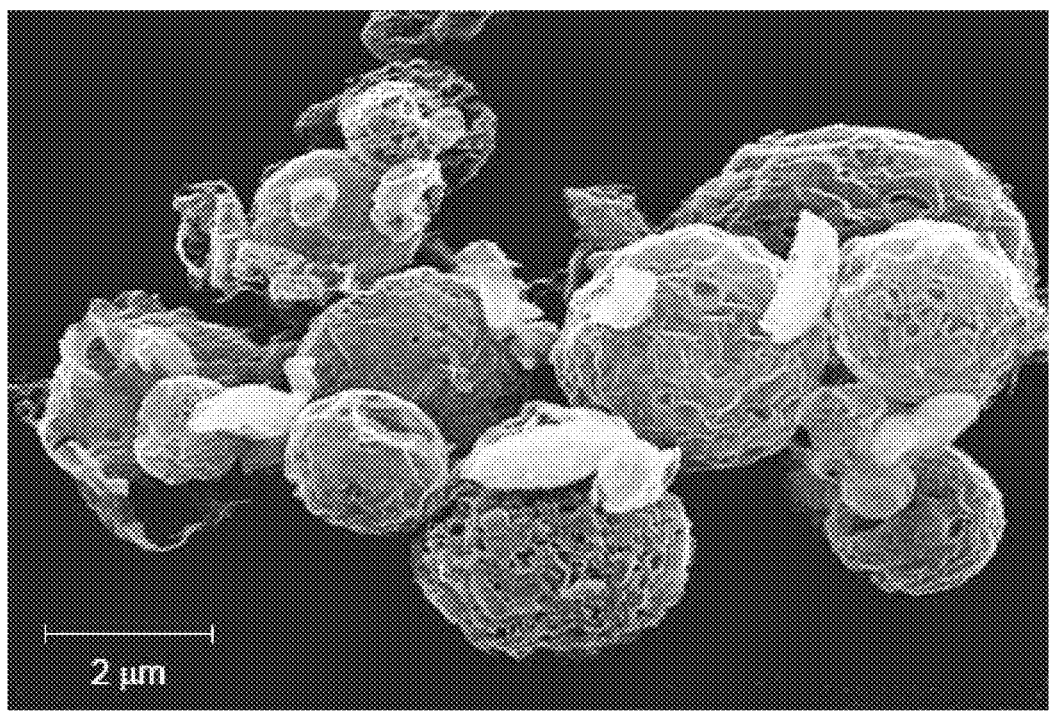
FIG. 1 is an SEM photomicrograph of the respirable agglomerates comprising indacaterol and mometasone drug substances with porous carrier particles, as described in Example 1 (Lot 11015A-6-7). The porous carrier particles are depicted in greyscale and drug crystals are shown in white.

Respirable agglomerates comprising indacaterol and mometasone drug substances were manufactured as described in Example 1 (Lot#11015A-6-7). FIG. 1 is an SEM photomicrograph of the respirable agglomerates comprising indacaterol and mometasone drug substances with small porous carrier particles. The crystals adhering to the porous particles are clearly evident in the photomicrograph. No evidence of free crystals is observed.

Example 3

Content Uniformity of Respirable Agglomerates

Respirable agglomerates comprising indacaterol acetate, mometasone furoate, and glycopyrronium bromide drug substances were manufactured as described in Example 1 (Lot#11015A-7-6). The bulk powder was filled into size 3 hypromellose capsules using a proprietary drum-based filling machine. The target fill mass was 2.5 mg. This was achieved with high accuracy and precision. The relative standard deviation (RSD) for the filling process was 2.4%.

Figure 2:
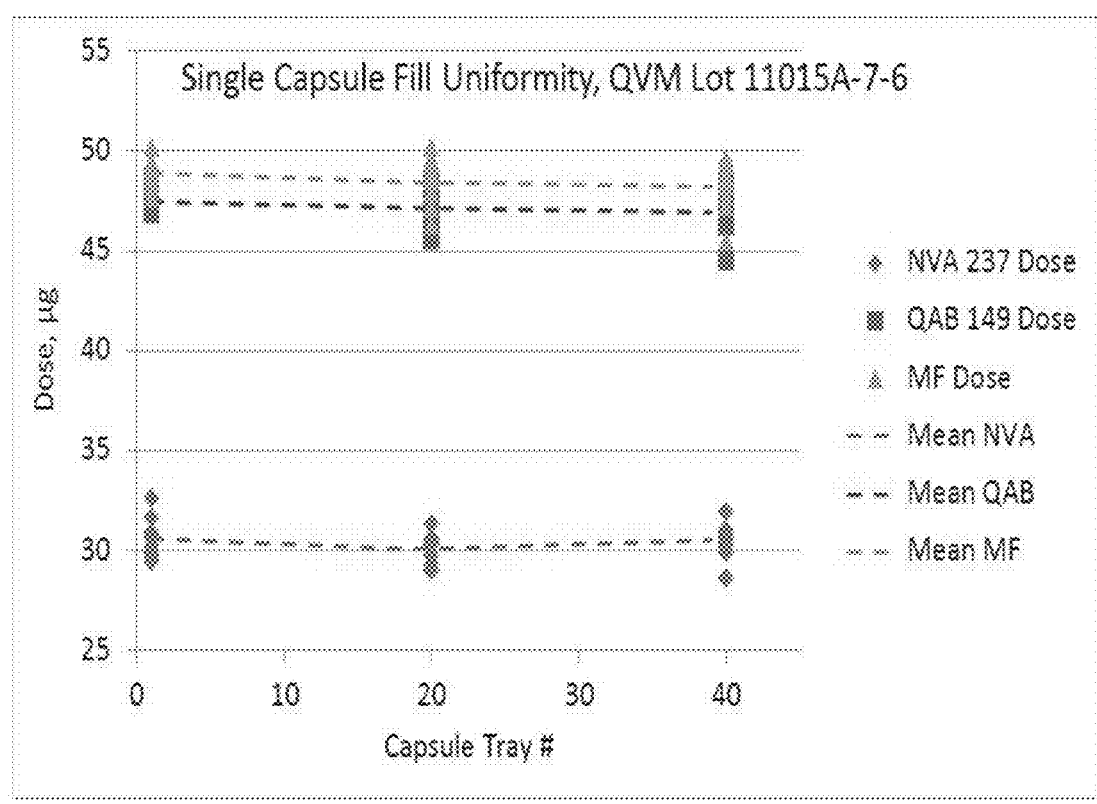
FIG. 2 is a graph showing dose content uniformity of a dry powder formulation comprising respirable agglomerates of indacaterol acetate, mometasone furoate, and glycopyrronium bromide and small porous carrier particles made according to Example 1 (Lot 11015A-7-6).

The drug content in the respirable agglomerates was determined by RP-HPLC. The variability in mean content for each of the three drugs is comparable to the variability in machine filling (Table 2). Moreover, there are no significant differences in content for capsules filled at the beginning, middle, and end of the batch. This indicates that: (a) there was a uniform suspension of drug crystals and porous particles in the anti-solvent; (b) there was no segregation of drug from carrier in the powder batch resulting from the filling process, as shown also by FIG. 2. Drug contents given in Table 2 are for the free drug.

Hence, the suspension of particles in the anti-solvent provides a novel method to achieve good mixing and uniformity of micron-sized drug and carrier particles in a bulk powder.

TABLE 2

Mean drug contents for indacaterol acetate, mometasone furoate and glycopyrronium bromide in ordered mixes with small porous particles

| Drug | Mean Drug Content (μg) | RSD (%) |
| --- | --- | --- |
| 2% w/w indacaterol acetate | 47.2 | 1.9 |
| 2% w/w mometasone furoate | 48.5 | 2.1 |
| 1.5% w/w glycopyrronium bromide | 30.4 | 2.9 |
| Bulk powder fill mass | 2500 | 2.4 |

Example 4

Delivered Dose Uniformity of Respirable Agglomerates

The delivered dose uniformity of respirable agglomerates comprising indacaterol acetate, mometasone furoate, glycopyrronium bromide crystals and small porous carrier particles (Lot 11015A-7-6) is presented in FIG. 3. The bulk powder was filled into size 3 hypromellose capsules. The capsules were then individually filled into a Concept1 dry powder inhaler (as described herein). The Concept1 Inhaler is a low resistance, capsule-based dry powder inhaler. The device was emptied at a flow rate of 60 L/min and an inhaled volume of 2 L onto a filter. The mass of each individual drug on the filter was quantitated by RP-HPLC. The total mass of powder on the filter was also determined gravimetrically.

The variability in the delivered dose is presented in Table 3. The mean delivered dose and variability in delivered dose is comparable for the three drugs in the respirable agglomerate. All of the components in the formulation pass the FDA Draft Guidance on delivered dose uniformity which stipulates that 90% of the delivered dose values must be within ±20% of the nominal dose (or label claim), with none outside of 25%. Hence, excellent delivered dose uniformity is observed for this complex triple combination product.

TABLE 3

Delivered dose uniformity for respirable agglomerates comprising indacaterol acetate, mometasone furoate, glycopyrronium bromide and small porous carrier particles delivered from the Concept1 dry powder inhaler

| | Indacaterol acetate | Mometasone furoate | Glycopyrronium bromide | Bulk powder |
| --- | --- | --- | --- | --- |
| Mean delivered dose (% nominal) | 83.5 | 84.8 | 82.1 | 91.0 |
| RSD | 4.8 | 4.9 | 4.3 | 4.4 |

The pattern in the variability for different capsules tested at the beginning, middle, and end of the filled batch (illustrated also in FIG. 3), are consistent for each of the drugs and consistent with the gravimetric emitted powder mass results across the batch. This provides additional strong evidence that the drugs are strongly associated with the small porous particle carrier, and remain so throughout the aerosolization process.

Example 5

Comparison of Aerodynamic Particle Size Distributions of Respirable Agglomerates with PulmoSpheres Particles and with Traditional Lactose Blend A comparison of the aerodynamic particle size distributions (APSD) of three formulations comprising indacaterol delivered with the Concept1 single dose dry powder inhaler is presented in Table 4 and FIG. 4. The APSD were determined on a Next Generation Impactor at a flow rate of 60 L/min. The first formulation tested was the currently marketed lactose blend comprising indacaterol maleate (Onbrez®, Novartis). The second formulation is a standard small porous particle formulation where the crystalline drug substance is coated with a porous matrix of phospholipid via spray drying an emulsion-based feedstock (PulmoSphere™ technology). Finally, the third formulation comprised respirable agglomerates in accordance with embodiments of the present invention, the respirable agglomerates comprising small porous carrier particles and micronized indacaterol acetate. The overall mass balance of the composition of the spray-dried formulations is similar, comprising the indacaterol drug substance and a 2:1 molar ratio of DSPC to calcium chloride. The MMAD of the respirable agglomerates is slightly larger than the standard porous particle formulation, yet the overall fine particle fraction, expressed as the percentage of the nominal dose on stage 3 to filter in the NGI remains very high, validating the usefulness of the formulation and process in being capable of efficaciously delivering multiple drug actives in fixed dose combinations.

These properties are further illustrated in FIG. 4 which is a comparison of the aerodynamic particle size distributions for indacaterol maleate formulations manufactured by the two prior art process and by an embodiment of the method and formulation of the present invention. Thus, composition and process embodiments of the present invention provide a respirable agglomerate fixed dose combination particle, wherein the respirable agglomerates comprise three different actives (with varying aqueous solubilities) and the respirable fraction ($FPF_{S3-F}$) remains high—comparable to that of a PulmoSphere particle.

TABLE 4

Comparison of the aerodynamic particle size distributions for indacaterol maleate formulations manufactured by three discrete processes

| Formulation | MMAD (μm) | FPF$_{S3\text{-}F}$ (% nominal) | Difference from standard PulmoSphere |
|---|---|---|---|
| Lactose blend (OnBrez) | 2.8 | 26.2 | −62.0% |
| Standard PulmoSphere | 2.8 | 68.9 | — |
| Respirable Agglomerate Lot# - 11015A-6-7 | 3.3 | 60.6 | −12.0% |

Example 6

Comparison of the Aerodynamic Particle Size Distributions of Mometasone in Mono, Combo (Double), and Triple ("Trombo") Formulations FIG. 5 and Table 5 provide a comparison of the aerodynamic particle size distributions of respirable agglomerate formulations comprising mometasone furoate as described in Example 1 delivered with the Concept1 dry powder inhaler at a flow rate of 60 L/min. The three respirable agglomerate formulations comprise the mono mometasone formulation (Lot #11015-7-1), its combination with indacaterol acetate (Lot #11015-7-4), and its triple combination with indacaterol acetate and glycopyrronium bromide (Lot #11015-7-6). These three formulations have comparable aerosol performance, as indicated by the close agreement in MMAD and FPF$_{S3\text{-}F}$. The variation in FPF$_{S3\text{-}F}$ for the combination products was within 5% of the value observed for the mono formulation. Thus, the in-vitro performance is within the ±15% required for equivalence between the three formulations, indicating that they pass the in vitro combination rule. A comparison is also made with the marketed Asmanex® formulation (Merck) delivered with the Twisthaler®, at a flow rate of 60 L/min. The FPF$_{S3\text{-}F}$ for the respirable agglomerate formulations was more than 4-fold higher than that observed for Asmanex, despite the fact that the MMAD of Asmanex is lower. This is a consequence of the bimodal versus unimodal particle size distribution for the lactose blend relative to the respirable agglomerates of the present invention.

TABLE 5

Aerosol performance of respirable agglomerates comprising mometasone furoate in comparison with the marketed Asmanex ® drug product

| Formulation | MMAD (μm) | FPF$_{S3\text{-}F}$ (% nominal) | Difference from mono |
|---|---|---|---|
| Mono (Lot # - 11015A-7-1) | 3.1 | 63.8 | — |
| Combo (with indacaterol acetate) (Lot # - 11015A-7-5) | 3.0 | 62.5 | −2.0% |
| Trombo (with indacaterol acetate and glycopyrronium bromide) (Lot # - 11015A-7-6) | 2.9 | 66.9 | +4.8% |
| Asmanex ® (Merck) | 2.6 | 15.2 | −76.2% |

Example 7

Preservation of the Physical Form of Indacaterol Acetate in Respirable Agglomerates When indacaterol acetate is suspended in an aqueous feedstock to be spray-dried, the drug substance rapidly disproportionates to form indacaterol free base and acetic acid. In the process of the present invention, an ordered mixture of micronized indacaterol acetate crystals and small porous particles are created by suspending the particles in a liquid perfluorocarbon, and then removing the liquid in a drying process. The physical form of the indacaterol acetate drug substance can be determined by X-ray powder diffraction (XRPD). FIG. 6 shows XRPD patterns for a series of powders. FIG. 6 (top) shows the characteristic XRPD pattern obtained for indacaterol free base, following disproportionation of suspended indacaterol acetate in water. FIG. 6 (middle) shows the XRPD pattern for indacaterol acetate suspended in perfluorooctyl bromide (PFOB). This is identical to the XRPD pattern found for indacaterol acetate drug substance (FIG. 6, bottom) showing that the salt form of the drug is maintained following dispersion in PFOB.

FIG. 7 shows XRPD patterns. The top curve shows the pattern for the indacaterol acetate drug substance, while the middle curve presents the XRPD pattern for respirable agglomerates of the present invention made according to Example 1—lot 227-74-2 of 7% w/w indacaterol acetate with small porous particles. The pattern is dominated by the characteristic phospholipid peak at 2θ=21°. The bottom curve of FIG. 7 represents the PulmoSphere (placebo) particles, and also shows the characteristic phospholipid peak. In the middle curve, the characteristic peaks associated with the salt form of indacaterol acetate are clearly evident, suggesting that the physical form of the indacaterol acetate drug substance is preserved through the nonaqueous manufacturing process. Peaks characteristic of indacaterol free base are not present. Similar results demonstrating the maintenance of the physical form of the indacaterol acetate drug substance were obtained with near infrared diffuse reflectance spectroscopy. Hence, the formation of respirable agglomerates via the nonaqueous manufacturing process presented herein provides a means to protect drugs that may be physically or chemically unstable in aqueous media from degradation.

Example 8

Aerosol Performance of Respirable Agglomerates in Concept1 and Genie Dry Powder Inhalers In this Example, the performance of a dry powder comprising a triple-combination of respirable agglomerates made in accordance with Example 1 (Lot #s 11015A-10-3, 11015A-10-4 and 11015A-10-5) were tested in a two different dry powder inhaler devices: Genie, an active, multidose, blister-based device, and Concept 1, a passive, unit dose, capsule-based device. The Genie device utilizes a piezoelectric element to actively fluidize and disperse the dry powder. The results are shown in Table 6. Also shown for comparative purposes are the results for a conventional PulmoSphere formulation of indacaterol maleate, and a lactose blend formulation of indacaterol maleate.

The fine particle dose less than 5 μm was determined by a drug specific HPLC method. The Concept1 was operated at a flow rate of 60 L/min, while the Genie device was operated at a flow rate of 36 L/min (4 kPa pressure drop).

TABLE 6

Aerosol performance of respirable agglomerates comprising a triple combination of indacaterol, glycopyrrolate, and mometasone in two inhaler devices: Concept1 and Genie

| | | FPF$_{<5\ \mu m}$, % (SD) | | |
|---|---|---|---|---|
| Lot # | Device | Indacaterol | Glycopyrrolate | Mometasone |
| 11015A-10-4 | Genie | 91.5 (3) | 62.0 (2) | 90.9 (3) |
| | Concept1 | 76.7 (1) | 48.4 (1) | 74.3 (1) |
| 11015a-10-5 | Genie | 66.3 (5) | 53.6 (6) | 69.9 (5) |
| | Concept1 | 70.9 (4) | 39.7 (3) | 69.5 (3) |
| SC0003 (Indacaterol PSph) | Genie | 60.1 | | |
| SC0002 (Indacaterol LB) | Genie | 30.8 | | |

The differences in FPF$_{<5\ \mu m}$ between indacaterol and mometasone relative to glycopyrrolate is reflective of the differences in the size of the micronized drug crystals present in the respirable agglomerates. For indacaterol and mometasone the drug crystals are small enough so that the aerodynamic properties of the respirable agglomerate are substantially controlled by properties of the small porous carrier particles. The x50 and x90 for micronized indacaterol acetate crystals were 1.63 μm and 3.08 μm, respectively. The x50 and x90 for micronized mometasone furoate crystals were 1.22 μm and 2.45 μm, respectively. In contrast, the larger sized crystals of glycopyrrolate utilized (x50=2.96 μm, x90=6.52 μm) has an impact on the size of the respirable agglomerates comprising the glycopyrrolate crystals, and the corresponding FPF$_{<5\ \mu m}$. It is worth noting that the FPF$_{<5\ \mu m}$ is significantly larger for the respirable agglomerates than is observed for traditional lactose blends, by a factor of 2-fold to 3-fold.

Example 9

Comparative Example of Dry Blending of Micronized Drugs and Small Porous Particles As noted herein the strong cohesion between fine drug particles results in difficulties with dry blending fine particles in the respirable size range. To further contrast the features, advantages and aspects of embodiments of the manufacturing process of the present invention (compared, for example, with Example 3), simple blends of micronized mometasone furoate crystals with small porous carrier particles were made on a Turbula® mixer. A Turbula mixer is a standard mixer utilized to make blends of coarse lactose with micronized drug particles. Following mixing on the Turbula, the bulk powder was sampled and the variability in content was assessed via RP-HPLC (Table 7). Poor accuracy and precision were observed for mometasone contents of less than 10% w/w, with measured RSD values between 21% and 38%. This example illustrates the difficulty encountered in forming stable, respirable blends of dry powders in the (size range from 1-5 microns) using standard powder mixing methods, and points to the utility of the anti-solvent evaporation method for forming the ordered mixture respirable agglomerates of embodiments of the present invention.

TABLE 7

Variability in content observed for micronized mometasone furoate blended with small porous carrier particles in a Turbula® mixer

| | Content % (w/w) MF Detected by HPLC | | |
|---|---|---|---|
| MF | Ave (% w/w) | Stdev | % RSD |
| 2 | 2.67 | 0.64 | 24.0 |
| 3.4 | 3.70 | 0.79 | 21.2 |
| 5.2 | 5.32 | 1.91 | 35.8 |
| 7.4 | 7.24 | 2.74 | 37.9 |
| 11.5 | 11.86 | 1.55 | 13.1 |
| 16.7 | 18.42 | 1.90 | 10.3 |

The invention claimed is:

1. A pharmaceutical composition for pulmonary delivery via a dry powder inhaler, the composition comprising a dry powder comprising a plurality of small porous carrier particles having a mass median diameter (MMD) of about 1-10 microns and a plurality of active agent particles having a MMD of less than about 4 microns, wherein the plurality of active agent particles are selected from the group consisting of particles of indacaterol or a pharmaceutically acceptable salt or ester thereof, particles of glycopyrronium or a pharmaceutically acceptable salt or ester thereof, and particles of mometasone or a pharmaceutically acceptable salt or ester thereof, and wherein the small porous carrier particles and the active agent particles form an ordered mixture of respirable agglomerates.

2. The pharmaceutical composition of claim 1 wherein the plurality of active agent particles comprise two different actives selected from the group consisting of particles of indacaterol or a pharmaceutically acceptable salt or ester thereof, particles of glycopyrronium or a pharmaceutically acceptable salt or ester thereof, and particles of mometasone or a pharmaceutically acceptable salt or ester thereof.

3. The pharmaceutical composition of claim 1 wherein the plurality of active agent particles comprise all three of:
   (i) active agent particles of indacaterol or a pharmaceutically acceptable salt or ester thereof; and
   (ii) active agent particles of glycopyrronium or a pharmaceutically acceptable salt or ester thereof; and
   (ii) active agent particles of mometasone or a pharmaceutically acceptable salt or ester thereof.

4. The pharmaceutical composition of claim 1 wherein the dry powder is characterized by a tap density of 0.03 to 0.5 g/cm$^3$, the small porous carrier particles comprise an MMD of about 1-5 microns, and the active agent particles comprise an MMD of less than about 3 microns.

5. The pharmaceutical composition of claim 1 wherein the dry powder is characterized by a fine particle fraction (FPF), expressed as a percentage of the nominal dose <3.3 μm (FPF<3.3 μm) of greater than about 40%.

6. The pharmaceutical composition of claim 1 wherein the dry powder is characterized by a fine particle fraction (FPF), expressed as a percentage of the nominal dose less than 4.7 μm (FPF<4.7 μm) of greater than about 50%.

7. The pharmaceutical composition of claim 1 wherein the dry powder is characterized by a lung deposition of at least 40% of a nominal dose.

8. The pharmaceutical composition of claim 1 wherein the dry powder is characterized by delivery from a passive dry powder inhaler substantially independently of a peak inspiratory flow rate.

9. The pharmaceutical composition of claim 1 wherein:
the plurality of small porous carrier particles have a geometric diameter of 2-3 microns, and consist essentially of distearoylphosphatidylcholine and calcium chloride; at least 50% of the active agent particles have a geometric diameter of less than 3 microns; and the dry powder is characterized by one or more of a tapped density of 0.03 to 0.5 g/cm$^3$ a mass median aerodynamic diameter (MMAD) of about 1 to 5 microns, and a FPF<4.7 μm of at least 50%.

10. The dry powder pharmaceutical composition of claim 2, wherein:
the porous carrier particles have a MMD of 1 to 5 microns;
at least 50% of the active agent particles comprising glycopyrronium or a pharmaceutically acceptable salt or ester thereof have a geometric diameter of 0.01-3 microns;
at least 50% of the active agent particles comprising indacaterol or a pharmaceutically acceptable salt or ester thereof have a geometric diameter of 0.01-3 microns;
at least 50% of the active agent particles comprising mometasone or a pharmaceutically acceptable salt or ester thereof have a geometric diameter of 0.01-3 microns;
wherein the active agent particles adhere to the carrier particle to form an ordered mixture of respirable agglomerate particles, and wherein the composition is characterized by a tapped density of 0.03 to 0.5 g/cm$^3$ and a FPF<4.7 μm of at least about 50%.

11. The dry powder formulation of claim 10, wherein
(i) the small porous carrier particles comprise a 2:1 molar ratio of distearoylphosphatidylcholine (DSPC) to CaCl$_2$ and are present in an amount of about 91-99%; and
(ii) wherein the particles of indacaterol or a pharmaceutically acceptable salt or ester thereof comprise indacaterol acetate, and wherein said particles are present in an amount of about 0.5-3% w/w; and
(iii) wherein the particles of glycopyrronium or a pharmaceutically acceptable salt or ester thereof comprise glycopyrronium bromide, and wherein said particles are present in an amount of about 0.5-3% w/w; and
(iv) wherein the particles of mometasone or a pharmaceutically acceptable salt or ester thereof comprise mometasone furoate, and wherein said particles are present in an amount of about 0.5-3% w/w.

12. An inhalation unit dosage form comprising a receptacle;
and the dry powder composition of claim 10 contained within the receptacle.

13. A process for making the dry powder formulation of respirable agglomerate particles of claim 1, the process comprising the steps of:
(a) preparing a first feedstock comprising a hydrophobic excipient dispersed in an aqueous liquid phase and spray-drying said first feedstock to provide a bulk powder composition comprising a plurality of small porous powder carrier particles;
(b) providing active agent particles of at least one of:
(i) particles of indacaterol or a pharmaceutically acceptable salt or ester thereof;
(ii) particles of glycopyrronium or a pharmaceutically acceptable salt or ester thereof; and
(iii) particles of mometasone or a pharmaceutically acceptable salt or ester thereof
wherein at least 50% of the active agent particles have a geometric diameter of less than 3 microns;
(c) preparing a second feedstock comprising a suspension of the carrier particles of step (a) and the drug particles of step (b) in a non-aqueous anti-solvent; and
(d) subjecting the second feedstock to a solvent removal process to yield a bulk powder formulation comprising an ordered mixture of respirable aggregate particles comprising small porous carrier particles and micronized drug particles, wherein the respirable agglomerate particles are characterized by a tapped density of 0.03 to 0.5 g/cm$^3$, and a FPF<4.7 μm of at least about 50%.

14. The process of claim 13 wherein the hydrophobic excipient comprises DSPC and calcium chloride.

15. The process of claim 14 wherein the step of providing active agent particles comprises providing at least two of:
(i) particles of indacaterol or a pharmaceutically acceptable salt or ester thereof;
(ii) particles of glycopyrronium or a pharmaceutically acceptable salt or ester thereof; and
(iii) particles of mometasone or a pharmaceutically acceptable salt or ester thereof.

16. The process of claim 14, wherein the step of providing active agent particles comprises providing all three of:
(i) particles of indacaterol or a pharmaceutically acceptable salt or ester thereof;
(ii) particles of glycopyrronium or a pharmaceutically acceptable salt or ester thereof; and
(iii) particles of mometasone or a pharmaceutically acceptable salt or ester thereof.

17. The process of claim 16, wherein:
(i) the indacaterol or pharmaceutically acceptable salt or ester thereof is indacaterol acetate;
(ii) the glycopyrronium or pharmaceutically acceptable salt or ester thereof is glycopyrronium bromide; and
(iii) the mometasone or pharmaceutically acceptable salt or ester thereof is mometasone furoate.

18. A method of treating a patient comprising administering, the dry powder formulation according to claim 1 to a patient in need thereof via a dry powder inhaler.

* * * * *